(12) United States Patent
Charych et al.

US007153682B2

(10) Patent No.: US 7,153,682 B2
(45) Date of Patent: Dec. 26, 2006

(54) MICROARRAYS ON MIRRORED SUBSTRATES FOR PERFORMING PROTEOMIC ANALYSES

(75) Inventors: Deborah Charych, Albany, CA (US); Eric Beausoleil, Paris (FR); Ronald N. Zuckermann, El Cerrito, CA (US)

(73) Assignee: Chiron Corporation, Emeryville, CA (US)

( * ) Notice: Subject to any disclaimer, the term of this patent is extended or adjusted under 35 U.S.C. 154(b) by 125 days.

(21) Appl. No.: 10/190,308

(22) Filed: Jul. 3, 2002

(65) Prior Publication Data

US 2003/0017508 A1   Jan. 23, 2003

Related U.S. Application Data

(63) Continuation-in-part of application No. 09/874,091, filed on Jun. 4, 2001.

(60) Provisional application No. 60/209,711, filed on Jun. 5, 2000.

(51) Int. Cl.
*C12M 1/34* (2006.01)
*C40B 40/00* (2006.01)
*C40B 40/10* (2006.01)
*G01N 33/53* (2006.01)
*C40B 50/18* (2006.01)

(52) U.S. Cl. .............. 435/287.8; 435/7.1; 435/287.1; 435/287.2; 435/288.7; 435/DIG. 34; 435/DIG. 35; 435/DIG. 36; 435/DIG. 40; 435/DIG. 43; 436/518; 436/524; 436/525; 436/527; 436/535

(58) Field of Classification Search .................. 435/4, 435/7.1, 287.1, 287.2, 810, 283.1, 287.8, 435/288.7, DIG. 1, DIG. 34, DIG. 35, DIG. 36, 435/DIG. 40, DIG. 43; 436/518, 524, 527, 436/535
See application file for complete search history.

(56) References Cited

U.S. PATENT DOCUMENTS

| | | | |
|---|---|---|---|
| 4,963,263 A | 10/1990 | Kauvar | |
| 5,091,318 A * | 2/1992 | Anawis et al. | ............... 436/513 |
| 5,133,866 A | 7/1992 | Kauvar | |
| 5,340,474 A | 8/1994 | Kauvar | |
| 5,409,611 A | 4/1995 | Kauvar | |
| 5,478,527 A | 12/1995 | Gustafson et al. | ....... 422/82.11 |
| 5,482,867 A | 1/1996 | Barrett et al. | ............... 436/518 |
| 5,556,942 A | 9/1996 | Kauvar et al. | |
| 5,567,317 A | 10/1996 | Kauvar | |
| 5,599,903 A | 2/1997 | Kauvar et al. | |
| 5,624,711 A | 4/1997 | Sundberg et al. | |
| 5,763,570 A | 6/1998 | Kauvar et al. | |
| 5,767,086 A | 6/1998 | Kauvar et al. | |
| 5,786,336 A | 7/1998 | Kauvar et al. | |
| 5,831,005 A | 11/1998 | Zuckerman et al. | |
| 5,831,070 A | 11/1998 | Pease et al. | |
| 5,955,432 A | 9/1999 | Kauvar et al. | |
| 5,965,695 A | 10/1999 | Simon et al. | |
| 6,013,462 A | 1/2000 | Kauvar et al. | |
| 6,329,209 B1 * | 12/2001 | Wagner et al. | ............... 436/518 |
| 6,406,921 B1 | 6/2002 | Wagner et al. | |

FOREIGN PATENT DOCUMENTS

| | | |
|---|---|---|
| DE | 197 41 716 A1 | 3/1999 |
| EP | 1 996 362 A1 | 6/2000 |
| WO | WO 89/09088 | 10/1989 |
| WO | WO 91/06356 | 5/1991 |
| WO | WO 92/10757 | 6/1992 |
| WO | WO 98/31839 | 7/1998 |
| WO | WO 98/42730 | 10/1998 |
| WO | WO 98/53304 | 11/1998 |
| WO | WO 98/59360 | 12/1998 |
| WO | WO 99/48897 | 9/1999 |
| WO | WO 00/11208 | 3/2000 |
| WO | WO 01/01142 | 1/2001 |
| WO | WO 01/94946 A | 12/2001 |

OTHER PUBLICATIONS

Hruby, et al., "Synthesis of oligopeptide and peptidomimetic libraries", Department of Chemistry, University of Arizona, Current Opinion in Chemical Biology, 1997, 1:114-119.

Ripka, et al., "Peptidomimetic design", Department of Chemistry and School of Pharmacy, University of Wisconsin-Madison, Current Opinion in Chemical Biology, 1998, 2:441-452.

Al-Obeidi, et al., "Peptide and Peptidomimetic Libraries", Molecular Diversity and Drug Design, Molecular Biotechnology, 1998, vol. 9, pp. 205-223.

Berry, et al., "Use of Antibody Fragments in Immunoaffinity Chromatography" Comparison of FV Fragments, VH Fragments and Paralog Peptides, Journal of Chromatography, Chrom. 23 869, 1992, pp. 239-245.

(Continued)

*Primary Examiner*—Peter Paras, Jr.
*Assistant Examiner*—My-Chau T Tran
(74) *Attorney, Agent, or Firm*—James E. Austin; Young J. Suh; Alisa A. Harbin

(57) ABSTRACT

Provided are peptidomimetic protein-binding arrays, their manufacture, use, and application. The protein-binding array elements of the invention include a peptidomimetic segment linked to a solid support via a stable anchor. The invention contemplates peptidomimetic array element library synthesis, distribution, and spotting of array elements onto solid planar substrates, labeling of complex protein mixtures, and the analysis of differential protein binding to the array. The invention also enables the enrichment or purification, and subsequent sequencing or structural analysis of proteins that are identified as differential by the array screen. Kits including proteomic microarrays in accordance with the present invention are also provided.

18 Claims, 14 Drawing Sheets

OTHER PUBLICATIONS

Chapman, et al., "Surveying for Surfaces that Resist the Absorption of Proteins", Department of Chemistry and Chemical Biology, Harvard University, Received Mar. 3, 2000, pp. 8303-8304.

Houry, et al., "Identification of in Vivo Substrates of the Chaperonin GroEL", Department of Cellular Biochemistry, Nature vol. 402, Nov. 11, 1999, pp. 147-154.

Kauvar, et al., "Paralog Chromatography", Research Report, Terrapin Technologies, Inc. and Rice University, vol. 8, No. 2, 1990, pp. 204-206.

Martzen, et al., "A Biochemical Genomics Approach for Identifying Genes by the Activity of Their Products", Reports, vol. 286, Nov. 5, 1999, pp. 1153-1155.

Rajur, et al., "Combinatorial Synthesis of N-Substituted α-Amino Acids on Sepharose" Lecture Programme and Abstract Book, Solid Phase Synthesis & Combinatorial Chemical Libraries, The European Peptide Society & BS/RSC Protein and Peptide Science Group, UK, Dates: Aug. 31-Sep. 4, 1999, Abstract.

"The Promise of Proteomics", Nature, Macmillian Magazines Ltd, Dec 16, 1999, vol. 402, Issue No. 402, p. 703.

Hruby, et al., "Synthesis of oligopeptide and peptidomimetic libraries", Department of Chemistry, University of Arizona, Current Opinion in Chemical Biology, 1997, 1:114-119.

Weetall, Preparation of immobilized proteins covalently coupled through silane coupling agents to inorganic support, 1993, vol. 41, 157-188.

"Redrawn Capillary Imaging Reservoir", Nov. 10, 1999, p. 1, abstract.

"Array for Generating Combinatorial Libraries", May 17, 2001, p. 1, abstract.

Falsey, et al., "Peptide and Small Molecule Microarray for High Throughput Cell Adhesion and Functional Arrays", UC Davis Cancer Center, Bioconjugate Chem., Received Nov. 21, 2000, vol. 12, No. 3, pp. 346-353.

MacBeath, et al., "Printing Proteins as Microarrays for High-Throughput Function Determination", Sep. 8, 2000, vol. 289, pp. 1760-1763.

Hergenrother, et al., "Small-Molecule Microarrays: Covalent Attachment and Screening of Alcohol-Containing Small Molecules on Glass Slides", Department of Chemistry and Chemical Biology, Received on Apr. 22, 2000, vol. 122, No. 32, pp. 7849-7850.

"Device for Carrying Out an Almost Simultaneous Synthesis of a Plurality of Samples", Dec. 29, 1999, p. 1, abstract.

"Surface Plasmon Resonance Sensor for the Simultaneous Measurement of a Plurality of Samples in Fluid Form", Nov. 25, 1999, p. 1, abstract.

"The Array for the High-Throughput Synthesis, Screening and Characterization of Combinatorial Libraries, and Methods for Making the Array", May 17, 2001, p. 1, abstract.

Zhu et al., "Global Analysis of Protein Activities Using Proteome Chips", Science, vol. 293, Sep. 14, 2001, pp. 2101-2105.

Fang, et al., "Membrane Protein Microarrays", JACS Communications, Biochemical Technologies, Science and Technology Division, vol. 124, No. 11, Received Oct. 22, 2001, Published on Web Feb. 26, 2002, pp. 2394-2395.

Mecklenburg, Michael, "XNA on Gold™ : a versatile microarray platform", pp. 61-62, poster abstract.

Haab, et al, "Protein microarrays for highly parallel detection and quantitation of specific proteins and antibodies in complex solutions", Genome Biology, vol. 2, No. 2, Received: Nov. 9, 2000, Revised: Dec. 5, 2000, Accepted: Dec. 13, 2000, pp. 0004.1-0004.13.

"The Promise of Proteomics", Nature, Macmillian Magazines Ltd, Dec. 16, 1999, vol. 402, Issue No. 402, p. 703.

MacBeth et al., "Printing Small Molecules as Microarrays and Detecting Protein—Ligand Interactions en Masse" J. Am. Chem. Soc. 121:7967-7968, 1999.

Pirrung et al., "A General Method for the Spatailly Defied Imobilization of Biomolecules on Glass Surface Using 'Caged' Biotin" Bioconjugate Chem. 7:317-321, 1996.

European Search Report dated Apr. 3, 2006 from related European Application No. 03763248.6—PCT/US-321127.

* cited by examiner

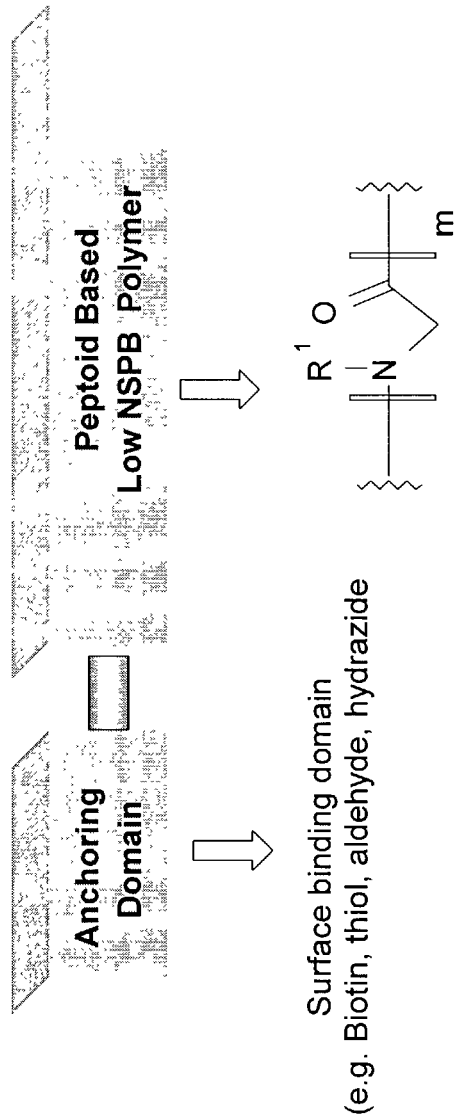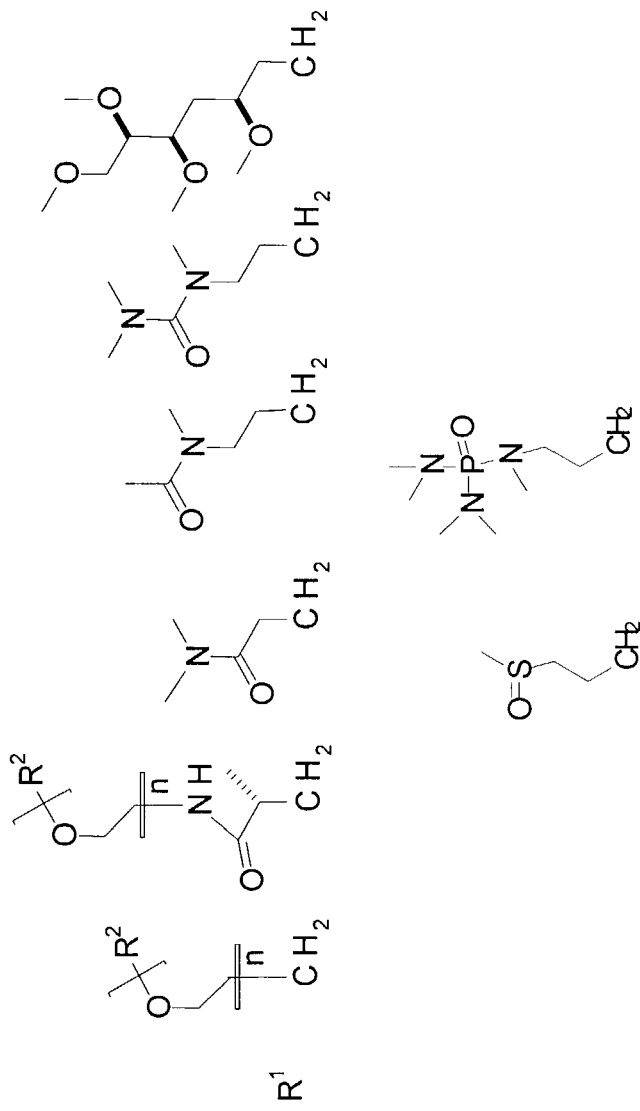
FIG. 3B

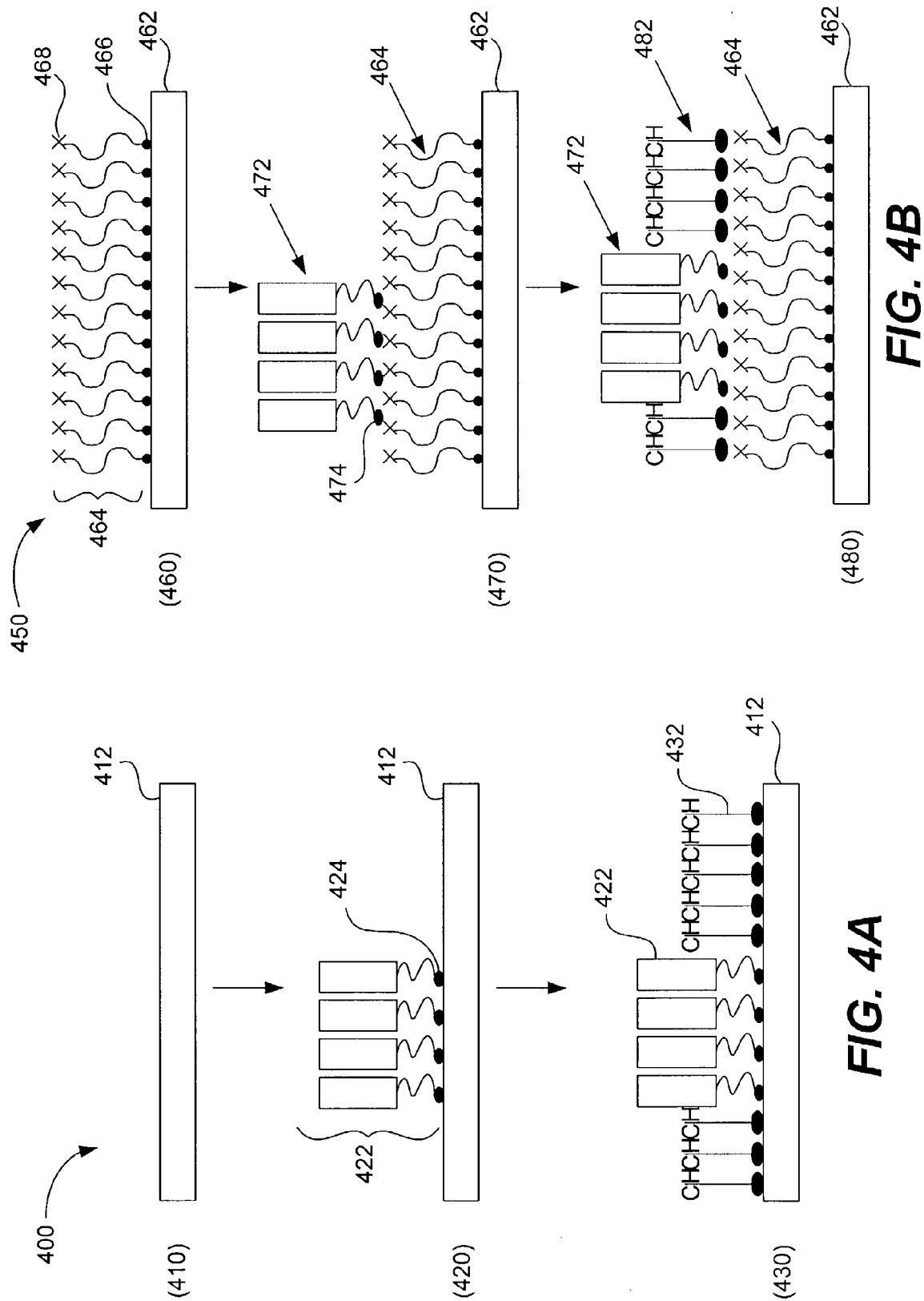

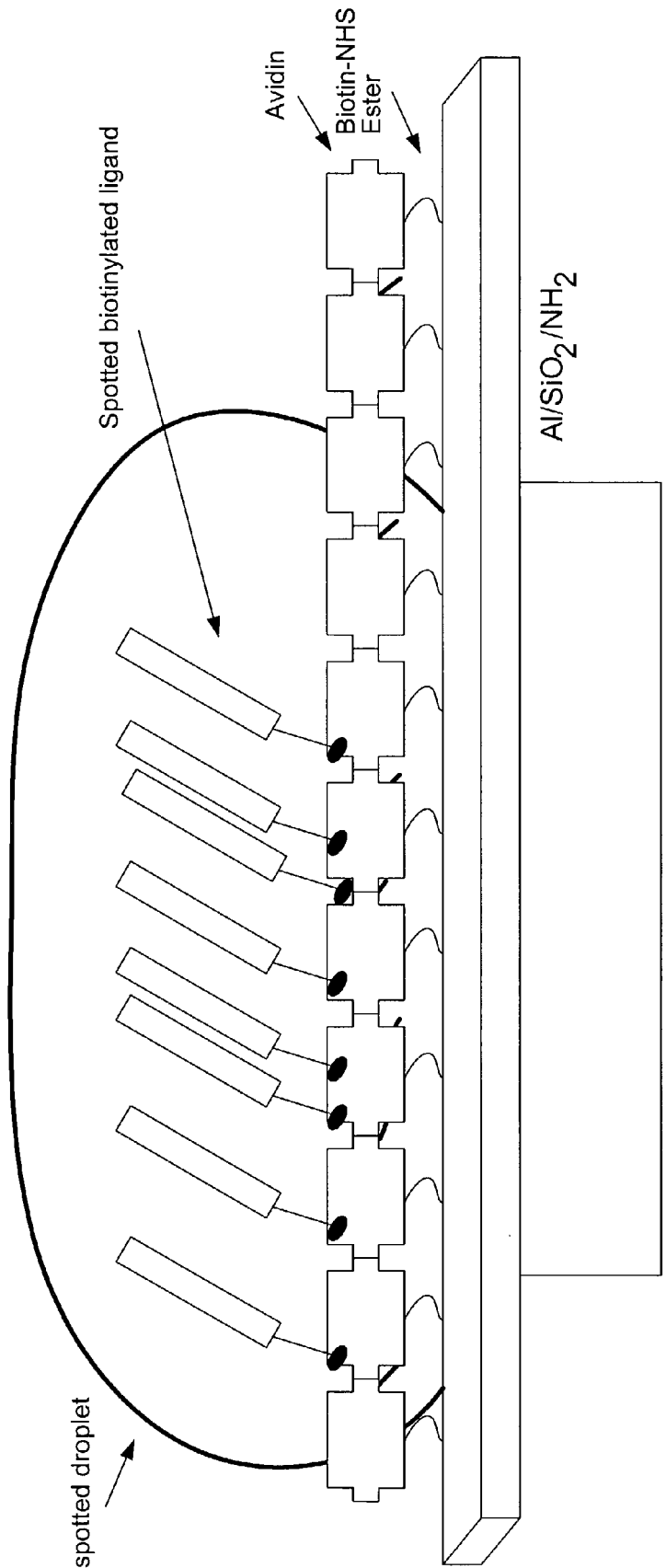
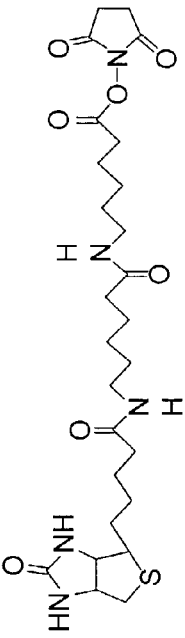
FIG. 7A
FIG. 7B

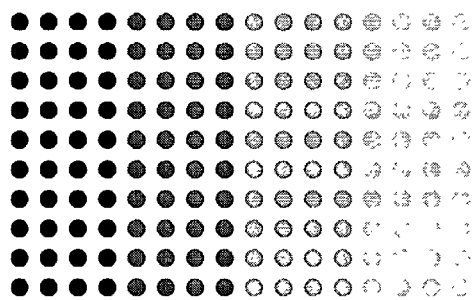
EYMPME-biotin anchor
Biotin/Avidin-derivatized surface
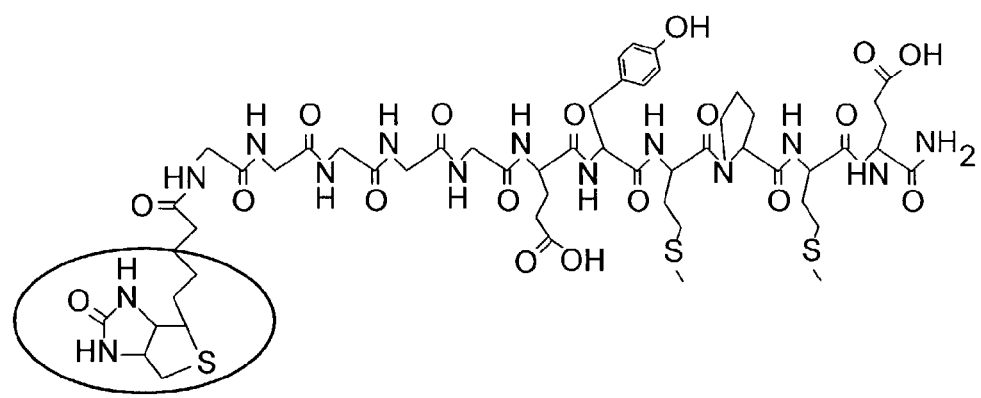
EYMPME-thiopropyl anchor
Maleimide-derivatized surface
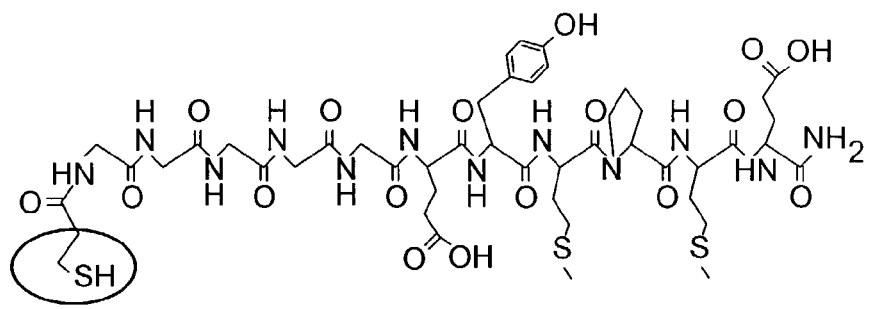
*FIG. 11*

Glass / APTES              Al / APTES
Cy5
Channel
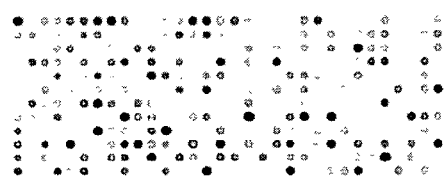
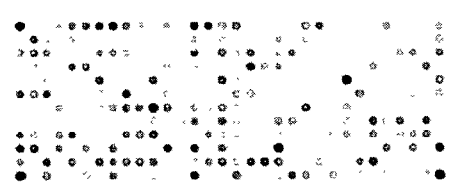
Cy3
Channel
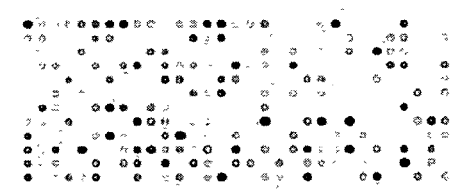
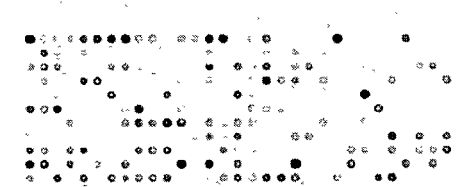
*FIG. 12*

MICROARRAYS ON MIRRORED SUBSTRATES FOR PERFORMING PROTEOMIC ANALYSES

CROSS-REFERENCE TO RELATED APPLICATIONS

This application is a continuation-in-part of U.S. patent application Ser. No. 09/874,091 titled MICROARRAYS FOR PERFORMING PROTEOMIC ANALYSES, filed Jun. 4, 2001; which claims priority from U.S. Provisional Application No. 60/209,711, entitled MICROARRAYS FOR PERFORMING PROTEOMIC ANALYSES, filed Jun. 5, 2000; the disclosure of each of which is incorporated by reference herein in its entirety for all purposes.

BACKGROUND OF THE INVENTION

The present invention relates to cell product analysis and materials. In one embodiment, the invention is directed to proteomic microarrays and methods of using them to conduct proteomic analyses.

In recent years, microarray technology has developed from a specialized subfield into an important tool for basic and applied studies in molecular biology, microbiology, pharmaceutics, agriculture, and many other biotechnologies. DNA microarray technology attempts to link the genome of an organism or cell to an expressed phenotype or protein function.

The overwhelming publication and patent literature on microarray technology describes arrays of DNA (or other forms of nucleic acid, such as cDNA or RNA), displayed on a solid surface such as a glass slide (often referred to as a "chip"). The arrayed DNA is typically in the form of short oligonucleotides (e.g., about 8 to 25 bases) or longer clones or PCR products (about 500 to 2000 bases). The former are typically synthesized on the solid support, whereas the latter are robotically "spotted" onto a solid support into an array format.

While there are reports of peptide and protein arrays on solid surfaces, these have received considerably less attention in comparison to DNA arrays. This is likely due to the inherent instability of these materials at interfaces, and in the presence of complex biological matrices. For example, it is well known, that many proteins denature upon contact with solid surfaces. Peptides, as well as proteins, are also subject to hydrolysis by any proteases that may be present in the biological sample being analyzed. In addition, peptide arrays are typically synthesized in-situ on solid surfaces using photolithographic methods. These techniques require the use of expensive custom-made masks that must be designed and manufactured for each chip. Furthermore, chemical characterization of surface-synthesized peptides is nearly impossible to perform due to the tiny amount of peptide generated.

Currently, the most common way of analyzing the proteome of biological samples employs two-dimensional ("2-D") gel electrophoresis. This method is problematic because the results are very sensitive to the experimental protocol (for example, development time of the gel as well as other parameters). Therefore, it is very difficult to get reproducible data from 2-D gels. Also, the sensitivity of the silver stain used in these gels is limited, and is less than that of the fluorescent labels used in microarray technologies.

Thus, there is an overwhelming need to develop effective microarray technology that is useful in a protein context. In many cases, functional pathways cannot be directly linked to a particular gene. Proteins often undergo a variety of post-translational modifications, interactions, or degradations that ultimately determine function. Even the seemingly simple evaluation of a protein's abundance cannot be directly correlated with the level of corresponding mRNA. The only solution is to evaluate the state of the cell, tissue or organism at the protein level. Therefore, a high throughput format that allows rapid display of protein differentials in complex mixtures such as cells, tissues, serum, etc., would provide a powerful counterpart and complement to DNA microarray technology.

SUMMARY OF THE INVENTION

To achieve the foregoing, the present invention provides peptidomimetic protein-binding arrays, their manufacture, use, and application. The protein-binding array elements of the invention include a peptidomimetic segment, an anchor segment and a linker segment connecting the peptidomimetic and anchor segment. The invention contemplates peptidomimetic array element library synthesis, distribution, and spotting of array elements onto solid planar substrates, labeling of complex protein mixtures, and the analysis of differential protein binding to the array. The invention also enables the enrichment or purification, and subsequent sequencing or structural analysis of proteins that are identified as differential by the array screen. Kits including proteomic microarrays in accordance with the present invention are also provided.

In one aspect, the invention pertains to an array of protein-binding agents stably attached to the mirrored surface of a solid support. The array includes a solid substrate having a substantially planar surface including an organic chemically-modified dielectric-coated reflective metal, and a plurality of different protein-binding agents bound to the substrate. Each of the protein-binding agents includes an anchoring segment stably bound to the substrate surface, a peptidomimetic protein-binding segment, and a linker segment connecting and separating the anchoring and peptidomimetic segments. The array may also include chemical blocking agents to prevent non-specific binding of proteins in samples run on the array.

In another aspect, the invention pertains to a method of making an array comprising a plurality of different protein-binding agents stably associated with the surface of a mirrored solid support. The method involves preparing for bonding a solid substrate having a substantially planar surface including an organic chemically-modified dielectric-coated reflective metal, and contacting a plurality of different protein-binding agents with the substrate under conditions sufficient for the protein-binding agents to become bound to the substrate surface. Each of the protein-binding agents includes an anchoring segment stably bound to the substrate surface, a peptidomimetic protein-binding segment, and a linker segment connecting and separating the anchoring and peptidomimetic segments. A chemical blocking agent designed to prevent non-specific binding of proteins in samples run on the array, may also be applied to the array.

These and other features and advantages of the present invention will be presented in more detail in the following specification of the invention and the accompanying figures which illustrate by way of example the principles of the invention.

BRIEF DESCRIPTION OF THE DRAWINGS

FIG. 3B illustrates a peptoid-based chemical blocking agent in accordance with the present invention designed to inhibit non-specific binding of proteins.

FIGS. 4A and 4B schematically depict alternative modes of binding a protein-binding agent to a solid support in accordance with one embodiment of the present invention.

FIG. 7A depicts the chemical formula for a NHS-LC-LC-biotin molecule used in a solution to coat aluminum slides to be used as a substrate in accordance with one embodiment of the present invention.

FIG. 7B depicts a representation of an avidin-derviatized aluminum slide spotted with a biotinylated protein-binding agent in accordance with one embodiment of the present invention.

FIG. 11 depicts the dependence of signal strength on the mode of surface attachment of a peptide for two modes of surface attachment in accordance with the present invention.

FIG. 12 depicts the difference in signal from glass vs. mirrored substrates in a comparative experiment to illustrate the advantages of mirrored substrate arrays in accordance with the present invention.

DESCRIPTION OF SPECIFIC EMBODIMENTS OF THE INVENTION

Figure 1A:
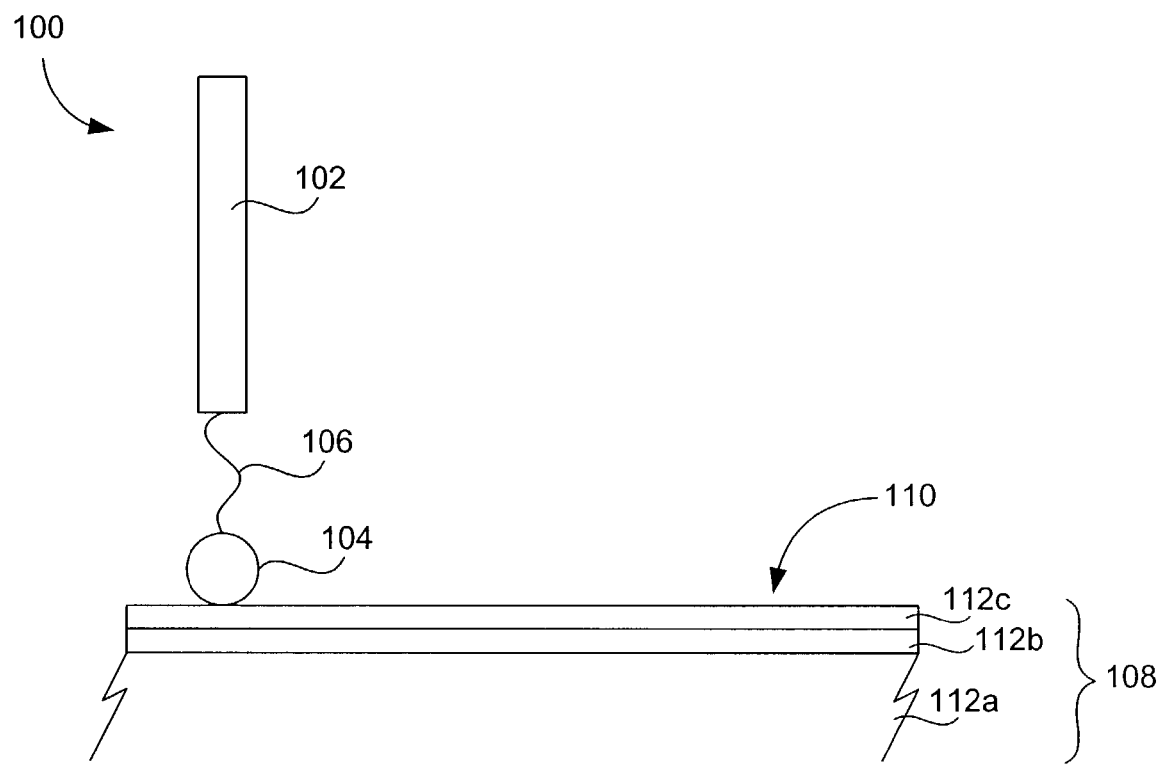
FIGS. 1A and 1B schematically depict the structure of a protein-binding agent array element and array portion, respectively, in accordance with one embodiment of the present invention.

The materials and associated techniques and apparatuses of the present invention will now be described with reference to several embodiments. Important properties and characteristics of the described embodiments are illustrated in the structures in the text and in the accompanying drawings. While the invention will be described in conjunction with these embodiments, it should be understood that the invention it is not intended to be limited to these embodiments. On the contrary, it is intended to cover alternatives, modifications, and equivalents as may be included within the spirit and scope of the invention. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Introduction

The present invention provides peptidomimetic protein-binding arrays, in addition to methods for their manufacture, use, and application. The protein-binding array elements of the invention include a peptidomimetic segment (an example of which is a peptoid), linked to a solid support using a stable anchor. In one embodiment, the invention provides peptidomimetic array element library synthesis, distribution, and spotting of array elements onto solid, planar substrates, labeling of complex protein mixtures, and the analysis of single protein binding or differential protein binding by contacting labeled pure protein or complex protein mixtures to the peptidomimetic array. Such analysis may lead to the identification of novel therapeutic targets involved in diseases such as cancer, HIV or diabetes. These novel targets can then be utilized in high throughput screening assays to find new drug candidates. The invention also enables the enrichment or purification, and subsequent sequencing or structural analysis, of proteins that are identified as differential by the array screen. The arrays can also be used to identify new synthetic ligands for proteins of interest (for protein purification or development of high throughput assays) or synthetic antigens for antibodies of interest. They may also be used to find new enzyme inhibitors or other high affinity ligands for drug targets, or as initial scaffolds for new therapeutics. Kits including proteomic microarrays in accordance with the present invention are also provided.

1. Protein-Binding Agent Arrays

Peptidomimetic arrays in accordance with the present invention are composed of a number of different array elements comprising protein-binding agents attached to the surface of a solid support. The different protein-binding agent array elements each include an anchoring segment attached to the substrate surface, a peptidomimetic protein-binding segment, and a linker segment connecting and separating the anchoring and peptidomimetic segments. A "peptidomimetic" as used herein refers to nonpeptide synthetic polymers or oligomers that detectably interact with proteins or receptors in a manner analogous to protein-protein or protein-peptide physical and/or chemical interactions under assay conditions. The anchoring segment is typically attached to the substrate surface such that the association between the anchoring group and the substrate surface, and thus the concentration and density of the protein-binding agent on the substrate surface, is maintained during the processing to which the microarray is subjected under its normal operating conditions, for example, as described herein. The number of different chemical species of protein-binding agent present on the surface of the array is at least 2, or at least 10, or at least 100, and can be much higher, generally being at least about 1,000, or at least about 5,000 to about 50,000, for example, between about 5,000 and about 10,000, as described further below.

Figure 1B:
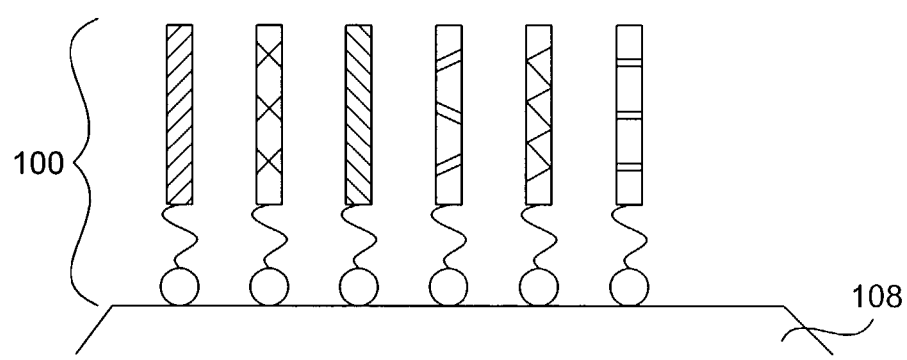

FIGS. 1A and 1B provide a representation of one such array element and an array in accordance with the invention. In FIG. 1A, a protein-binding array element 100 includes three segments: a peptidomimetic segment 102, an anchor segment 104, and a linker segment 106. The array element is attached to a solid support or substrate 108 by a bond between its anchor segment 104 and the substrate surface 110. In some cases, the substrate may be composed of a plurality of layers 112a, 112b, 122c forming a laminate. In FIG. 1B, a protein-binding array includes a plurality of different array elements 100, such as illustrated in FIG. 1A, attached to a planar substrate 108. Each of these components of the array is described in greater detail separately below.

A. Substrate

The solid support (FIGS. 1A and 1B, element 108) employed in arrays in accordance with the present invention may vary greatly depending on the intended use of the product to be produced. The solid support may be any suitable material for binding the protein-binding agent that is also compatible with any analytical methods with which the array is to be used. Compatibility can be determined using methods and materials known to those having skill in the surface or materials chemistry arts. In one embodiment, the solid support comprises an impermeable, rigid material. Suitable materials include plastics, such as polymers, e.g. polyvinylchloride, polyethylene, polystyrenes, polyacrylates, polycarbonate and copolymers thereof, e.g., vinyl chloride/propylene polymer, vinyl chloride/vinyl acetate polymer, styrenic copolymers, and the like. Suitable materials also include glasses, such as those formed from quartz, or silicon; and metals (including alloys), e.g., gold, platinum, silver, copper, aluminum, titanium, chromium and the like.

As noted above, in many embodiments of interest, the support or substrate 108 will be a composite of two or more different layers of material, where the composition includes at least a base material, e.g., as represented by element 112a in FIG. 1A, and one or more surface coating materials, as represented by elements 112b and 112c in FIG. 1A. For example, one embodiment of interest includes a base material 112a, such as a glass, which is coated with a metallic layer 112b, e.g., gold or aluminum overcoated with silicon dioxide, or titanium overcoated with silicon dioxide, and a functionalized organic, e.g., amino-modified thiol or amino-modified silane, layer 112c. The planar solid support may be in the dimensions of a standard 3"×1" microscope slide or in the shape of a 3" or 5" diameter circular wafer, for example. Other configurations will be apparent to those having skill in the surface or materials chemistry arts.

The solid support material or substrate may have a variety of different configurations, depending on the intended use of the material. Thus, in the broadest sense the support or base material may be in the form of a plate, sheet, cone, tube, well, bead, nanoparticle (e.g., about 5–100 nm), wafer, etc. In some embodiments, the base support material is one that has at least one substantially planar surface, e.g., as found on a plate, slide, sheet, disc, etc. In these embodiments, supports having an overall slide or plate configuration, such as a rectangular or disc configuration are employed.

In the planar, rectangular embodiments of the above-described slides, the length of the support will generally be at least about 1 cm and may be as great as about 40 cm or more, but will usually not exceed about 30 cm and may often not exceed about 20 cm. The width of support will generally be at least about 1 cm and may be as great as about 40 cm, but will usually not exceed about 30 cm and will often not exceed about 20 cm. The height of the support will generally range from about 0.01 mm to about 10 mm, depending at least in part on the material from which the rigid substrate is fabricated and the thickness of the material required to provide the requisite rigidity. Of particular interest in many embodiments are supports having the dimensions of a standard microscope slide. One typical substrate size is about 2.54 cm×7.62 cm and about 1–2 mm thick. However, any suitable dimensions can be employed.

Where the support is a bead, nanoparticle or microparticle, the diameter of the support typically ranges from about 5 nm to about 1000μ, particularly from about 10 nm to about 500μ.

The protein-binding agents can either be attached directly to the inorganic solid surface of layers 112a or 112b (as illustrated and described in more detail below with reference to FIG. 4A) or attached using the functionalized organic layer of 112c (as illustrated and described in more detail below with reference to FIG. 4B). In the latter case, the non-substrate-bound termini of the organic molecules in the layer are functionalized with a reactive group that can attach to the anchoring group of a subsequently bound protein-binding agent. Suitable terminal reactive groups may be, for example, maleimide, hydrazide, aminooxy, an activated ester such as N-hydroxysuccinimide, anhydride, aldehyde, disulfide, thiol, azide, phosphine or avidin, streptavidin, neutravidin or other altered forms of the protein avidin that bind biotin, depending upon the anchor's functional group.

In those embodiments in which the surface of the base support material, such as glass, is coated with a thin layer of a metal, such as aluminum, gold, or titanium, the thickness of the metal layer will generally range from about 300 Å to about 10,000 Å, more particularly from about 750 Å to about 2,000 Å, and still more particularly from about 1,000 Å to about 1,500 Å. The metal layer may be deposited on the substrate surface using any suitable protocol, including e-beam deposition, vapor deposition, sputtering and the like, as are known to those of skill in the art. An adhesion metal layer may be present between the metal layer and the substrate, where adhesion metals of interest include titanium, chromium, and the like. When present, the adhesion metal layer will typically range in thickness between about 5 Å and about 100 Å, usually between about 25 Å and about 75 Å and in many embodiments will be about 50 Å. In some embodiments, the above-described adhesion layer can be a molecular adhesion layer. Examples of materials suitable for forming molecular adhesion layers in accordance with the present invention include mercaptopropyltriethyoxysilane, and other mercaptoalkoxysilanes, such as mercaptopropyltrimethoxysilane, mercaptopropyltrichlorosilane, or other chain lengths such as mercaptohexyltriethoxysilane and other mercaptohexylalkoxysilanes, as are known in the art. Where the adhesion layer is a molecular adhesion layer, the thickness of the adhesion layer typically ranges from about 5 Å to about 50 Å.

The anchoring group of a protein-binding agent may be used to directly bond the protein-binding agent to an inorganic, e.g., metal or glass, substrate surface. For example, a thiol anchoring group may be used to bond directly to metals such as gold silver, copper or platinum without an intervening functionalized layer (e.g., maleimide/amine/thiol). Or, if the anchor group is an activated silane (i.e., modified to be reactive with other organic species, for example, hydrolyzable silane or modified silane that can condense with hydroxyls or other silanes to form siloxane bonds), e.g., chlorosilane or an alkoxysilane, the protein-binding agent can be directly bonded to glass or other oxide surfaces, such as titanium oxide, silicon oxide or aluminum oxide. Other activated silanes for this purpose include triethoxysilane, trichlorosilane, trimethoxysilane or other trialkoxysilanes. Within each of the classes, chain lengths may be from three atoms up to about eighteen atoms, for example.

Figure 1C:
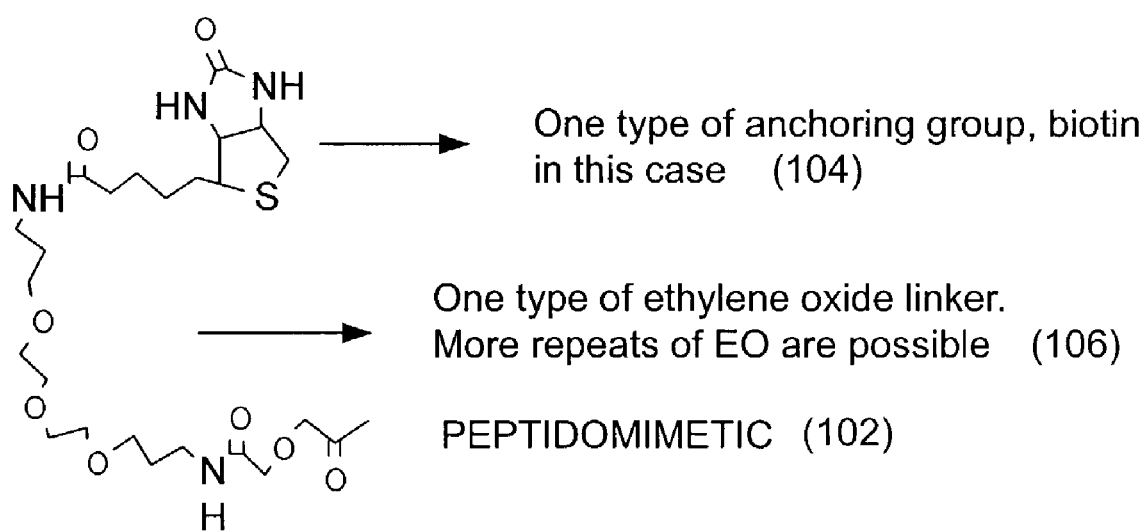
FIG. 1C depicts the molecular structure a protein-binding agent linking segment composed of ethylene oxides in accordance with one embodiment of the present invention.

As will be described in more detail below, in the case of bonding of the protein-binding agent directly to a substrate's inorganic surface, the protein-binding agent's linking segment (between the peptidomimetic and the anchor) should be long enough to keep the peptidomimetic sufficiently far from the hard substrate surface that the surface does not interfere with protein binding occurring (subsequently) at the peptidomimetic. The length can be from about 2 atoms to about 200 atoms, or about 2 Angstroms to about 300 Angstroms, for example. A typical linking segment may have a backbone of between about 2 to about 30 atoms, preferably about 6 to about 12 atoms. The linking segment may be composed of, for example, suitably derivatized aliphatic chains (e.g., aminoalkanoic acids, such as aminohexanoic acid), ethylene oxides (e.g., such as shown in FIG. 1C), sulfoxides, or "non-binding" (orthogonal) short peptoid or peptide elements that remain constant for each element of the array (e.g., a glycine heptamer), or some combination of these components.

As noted above, the protein-binding agents may also be attached using a functionalized organic layer (FIG. 1A, element 112c), such as an amino-modified thiol (aminothiol) (for use with some metal substrate surfaces) or an amino-modified silane (aminosilane) (for use with glass, metallic or other oxide substrate surfaces). Where such an organic layer is used, the termini of the organic molecules of the layer are functionalized with a reactive group that can stably attach to the substrate surface at on end, and to the anchor segment of a subsequently-bound protein-binding agent in accordance with the present invention at another end. Suitable terminal groups include, for example, maleimide which can form a covalent bond upon reaction with a thiol presented in the anchor. A further advantage of such synthetic anchoring systems is their stability, conferring long shelf life. Other possible terminal groups on the substrate include hydrazide, which can react to form covalent bonds with aldehyde or ketone moieties in the anchor; aminooxy, which can react to form covalent bonds with ketone moieties in the anchor, aldehyde, disulfide, thiol, azide, phosphine.

In another implementation, proteins such as avidin, streptavidin, or other analogs may be used as a coating for the solid support. In this case, biotin is used as the anchoring moiety of the protein-binding agent to form a stable, non-covalent bonding complex with avidin on the surface. Without wishing to be bound by any particular theory of action, it is believed that this format displays the protein-binding agent in a particularly biocompatible environment with desirable distances between display molecules and their neighbors, and desirable distances between display molecules and the solid surface. Other protein-coatings can also be employed, provided they sufficiently bind a small molecule anchoring group. These may include anti-digoxigenin/digoxigenin, anti-dinitrophenol/dinitrophenol, or many other protein/small molecule pairs known in the art. Avidin/biotin is of particular value because of it's extremely stable binding interaction. In addition, substantial signal increases have been observed for biotin/avidin immobilization compared to other suitable immobilization techniques in accordance with the present invention, for example 1000× higher than thiol/maleimide. Suitable synthetic macromolecules may also be used as mimics of such protein spacers. These may include high molecular weight polymers such as polyethyleneimines, dendrimers, polyacrylic acids, polylysines and the like.

Of course, other suitable binding combinations of this character (namely, as noted above, sufficiently stable to maintain the bond during the processing to which the microarray is subjected under its normal operating conditions) are also possible. In addition, those having skill in the surface chemistry arts will understand that the above-listed anchoring groups on the peptoid can function as reactive groups on the surface, and the reactive surface groups can also function as a peptidomimetic anchoring groups.

In one embodiment of the present invention, aluminum slides may be coated with a layer of silicon dioxide or silicon monoxide having a thickness of between about 500 Å to about 2,000 Å. The thickness is chosen to roughly correspond to ¼ the wavelength of the emission or excitation light. A layer of an aminoalkyl trialkoxysilane, such as aminopropyl triethoxysilane (APS), trichlorosilane, trimethoxysilane, and any other trialkoxysilane is coated on the surface of the oxide. In addition, other amino-silanes could also be used, for example, compounds having longer alkyl groups, such as octyl, decyl, hexadecyl, etc., that may form more ordered silane layers as will be appreciated by those having skill in the surface chemistry arts. The thickness of this silane layer may be from about 3 Å to about 100 Å, more preferably about 5 Å to about 50 Å, even more preferably about 7 Å to about 20 Å. One suitable example is an APS layer that is about 7 Å thick. The amino-modified Al surfaces may be functionalized with a reactive group that will bind to the anchor functional group on a protein-binding agent. In one embodiment, the functional group may be maleimide. In another embodiment, the functional group may be a whole protein such as avidin. An implementation of an avidin-presenting substrate is described with reference to FIGS. 7A and 7B in Example 3, below.

In another embodiment, a gold-surfaced substrate slide (or a slide surfaced with any metal capable of forming metal-thiol bonds, such as Ag, Pt, or Cu) may be coated with an aminothiol layer that is functionalized with a group that will bind to the anchor functional group on a protein-binding agent, such as maleimide. However, the anchor functional group and the surface-bound reactive group should be chosen to have orthogonal reactivities. As noted above, these anchor and substrate-bound groups can be interchanged as will be readily understood by those skilled in the art.

In general, the functionalized organic layer 112c is characterized by having a substantially uniform hydrophilic surface. By uniform is meant that the surface of the layer includes substantially no irregularities, such as gaps, pinholes, etc. The thickness of the layer 112c may vary considerably, where the thickness may be less than about 5,000 Å, usually less than about 2,000 Å, but can be much lower, particularly from about 5 Å to about 100 Å, or between about 20 Å to about 50 Å.

In at least those embodiments where the support material includes a metallic layer beneath a functionalized organic layer, e.g., where the support material is an amino-modified thiol layer on a gold coated microscope slide as described above, the thickness of the organic layer is chosen such that the layer 112c is at least sufficiently thick to separate any fluorescently labeled moiety that may be present to the surface a sufficient distance from the metallic layer on the substrate surface such that significant signal quenching (i.e., signal quenching of sufficient magnitude to effectively preclude meaningful detection of the signal) does not occur. In these embodiments, the functionalized organic layer may have a thickness that is at least about 30 Å, usually at least about 50 Å and more usually at least about 100 Å. Alternatively, in cases where quenching does occur, the slide may be treated with a high salt solution such as 0.75 M sodium chloride, 0.085 M sodium citrate (see. e.g., PCT Publication No. WO 01/01142).

In those embodiments where the array is employed with fluorescently labeled target, as described in greater detail below, the thickness of the functionalized amino-modified thiol layer may be chosen to provide for maximum amplification of the emitted and reflected signals. See e.g., U.S. Pat. No. 5,055,265, the disclosure of which is herein incorporated by reference. In such embodiments, the thickness of the organic layer will be about ¼ of the wavelength of the emitted light from the label. While the exact thickness of the organic layer will vary depending on the particular label with which it is to be employed, the thickness generally ranges from about 50 Å to about 300 Å, usually from about 100 Å to about 200 Å and more usually from about 125 Å to about 150 Å.

In one embodiment, the functionalized amino-modified thiol layer $112c$ includes at least one self-assembled monolayer (SAM). As such, the functionalized organic layer may include one or more different self-assembled monolayers grafted sequentially onto each other, where when the layer includes more than one self-assembled monolayer (see. e.g., PCT Publication No. WO 01/01142).

Among the substrates described above are some having reflective metal (e.g., aluminum, gold, etc.) surfaces ("mirrored substrates"). As noted above, a suitable substrate for use in arrays in accordance with the present invention will have a dielectric coated mirrored surface. The substrate will generally be a composite of a plurality of different layers of material, where the composition includes a base rigid, substantially planar solid support material, and a plurality of layers on the solid support. The solid support has (in the case of a reflective metal) or is coated with a reflective metal layer. By reflective metal it is meant a metal that reflects at least 90% incident light in the wavelength region of interest, generally visible (400–800 nm), and possibly including longer wavelengths in the near infrared, such as 800–1100 nm, with very little (at or near 0%) light refracted into the medium. Suitable examples include aluminum, chromium, copper, gold, silver, platinum, titanium, rhodium, etc.

The reflective metal is overcoated with a dielectric, e.g., silicon oxide or silicon dioxide (silica) or alumina or fluoride such as MgF2 or titanium dioxide. Silicon dioxide is preferred in many embodiments. The thickness of this layer can be adjusted to optimize the signal from the fluorescing species, as described in further detail in International Patent Application No. WO 98/53304, incorporated by reference herein for all purposes. The dielectric layer (e.g., silicon dioxide) is functionalized with a bifunctional organic surface layer, e.g., an amino-modified silane, suitable to facilitate the attachment of an array element 100 to the substrate 106. Suitable aluminum/oxide/amino-propyl silane (APS) coated glass slides are commercially available from Amersham-Pharmacia, Amersham, England.

As described below in Example 10, these mirrored substrates have been found to have performance benefits, particularly in terms of increased sensitivity, relative to more conventional glass slide substrates.

B. Protein-Binding Agents

As noted above, the protein-binding agents of the present invention are composed of three segments: a peptidomimetic, an anchor, and a linker connecting the peptidomimetic and the anchor.

A "peptidomimetic" as used herein refers to nonpeptide synthetic polymers or oligomers that detectably interact with proteins or receptors in a manner analogous to protein-protein or protein-peptide physical chemical interactions under assay conditions. Peptidomimetics are generally protease-resistant, and include, for example, oligomeric species such as peptoids, beta-peptides, and others as described in A. E. Barron & R. N. Zuckermann, *Bioinspired polymeric materials: in-between proteins and plastics*, Curr Opin Chem Biol 1999, 3(6):681–7 and K Kirchenbaum, R. N. Zuckermann and K. A. Dill, *Designing polymers the mimic biomolecules*, Curr Opin Chem Biol 1999 9(4):530–5, each of which is incorporated by reference herein in its entirety for all purposes, and constrained cyclic molecules such as cyclic peptides and heterocyles. In some cases, the peptidomimetic may also mimic the folding of natural proteins. Peptidomimetics in accordance with the present invention comprise generally no more than about 500 mers, more particularly no more than about 100 mers, typically no more than about 50 mers, and usually about 10 to about 20 mers, more particularly about 12 to about 16 mers. Given the parameters provided herein, one of skill in the art would be able to choose an appropriate peptidomimetic length for a given application without undue experimentation.

Examples of peptidomimetic libraries and their design and synthesis may be found in Fahad Al-Obeidi, et al., *Peptide and Peptidomimetic Libraries*, Molecular Biotechnology 1998, 9: 205–223; Victor J. Hruby et al., *Synthesis of oligopeptide and peptidomimetic libraries*, Curr Opin Chem Biol 1997, 1:114–119; and Amy S. Ripka et al., *Peptidomimetic Design*, Curr Opin Chem Biol 1998, 2:441–452, incorporated by reference herein in its entirety for all purposes.

In a preferred embodiment of the present invention, the peptidomimetic segment of the protein-binding agent is a peptoid. The term "peptoid" as used herein refers to polymers comprising N-substituted amides as described in U.S. Pat. Nos. 5,831,005, 5,877,278, 5,977,301, 5,871,387, 5,986,695, and 5,719,049; and in co-pending U.S. patent applications Ser. Nos. 08/340,073, 08/836,167, 08/920,205, 08/126,539, 08/277,228, 08/454,511, 08/485,106, 09/132, 828, 08/484,923, 09/704,422; and PCT Publications Serial Nos. 96/15143 and 93/09117, each of which is incorporated herein by reference in its entirety and for all purposes.

The anchoring segment provides for the stable attachment of the array element to the solid surface. This functional group is chosen to be reactive towards a complementary group that is displayed on the solid surface and orthogonal to (i.e., substantially non-reactive with) sidechains present in the ligand. An important feature of the anchoring group is that its reaction to the surface be sufficiently facile so that it is complete within the average lifetime of a droplet that is deposited by the robotic array spotter onto the surface. For example, if the surface displays a maleimide, a suitable anchoring group is a thiol and approximately 15–20 minutes at about 60% humidity are required for completion of the binding reaction before the approximately 10 nL drop evaporates. Of course, droplet lifetime varies with temperature, humidity and other conditions, allowing more or less time for the reaction to take place. As noted above, other surface display/anchor combinations are possible, including a hydrazide surface group with an aldehyde or ketone anchoring group. Or, the anchoring group can also be a biotin molecule, that will attach strongly (yet non-covalently) to a surface that displays an avidin protein.

The anchoring group may be attached to the peptidomimetic at either end (in the case of a peptoid, at either the C- or N-terminus). It can be attached either as a submonomer (e.g., a substituted amine), or as a modification of a peptidomimetic (e.g., peptoid) side chain after synthesis. Alternatively, in another example, the anchoring group may be present as a linker connecting the peptoid to a beaded solid support upon which it is synthesized. This linker may be cleaved from the resin along with the peptoid, to provide a readily available anchoring group. Some examples are described in co-pending U.S. patent application Ser. No. 60/282,115, titled *Peptoids Incorporating Chemoselective Functionalities*, filed Apr. 6, 2001, which is incorporated herein by reference in its entirety and for all purposes.

The linking segment of the protein-binding agent molecule is chosen to provide for separation between the solid surface and the peptidomimetic segment sufficient to facilitate interaction between the peptidomimetic and the components of the analyte solution (solution with which the microarray will be contacted), for example by providing separation between the substrate surface and the peptidomimetic so that the surface does not interfere with protein binding occurring (subsequently) at the peptidomimetic access for a protein binding site to the peptidomimetic ligand displayed on the surface, especially for proteins with deep binding pockets. The linker may also serve to separate the peptidomimetics on the surface from each other, thereby mitigating possible steric hindrance between the ligand and protein binding pocket. A typical linking segment may have a backbone of between about 2 to about 200 atoms, preferably about 6 to about 30 atoms. The linking segment may be composed of, for example, aliphatic chains (e.g., aminoalkanoic acids, such as aminohexanoic acid), ethylene oxides, sulfoxides, or "non-binding" ("orthogonal") short peptoid or peptide elements that remain constant for each element of the array, or some combination of these components. In one embodiment, a 2-carbon linker may be used. In another embodiment, three ethylene oxides may be used. An example of a non-binding short peptoid is a 2-mer to 12-mer, for example a 4-mer of methoxyethyl side chains that remain constant for each protein binding agent, while the peptidomimetic segment is variable. A suitable orthogonal peptide linker is a 2-mer to 12-mer, for example a 5-mer of glycine.

In some embodiments, where an organic layer is present on the substrate surface, a spacer functionality may be built into the organic layer. In such cases, the spacer in the substrate surface layer and the linker in the protein-binding agent may collectively contribute to the desired spacing of the peptidomimetic from the hard substrate surface. Further, the mitigation of steric hindrance may also be achieved by the selection of a surface coating that presents a particularly biocompatible format, such as an avidin protein (coupled with a biotin anchoring group on the protein-binding agent).

Figure 3A:
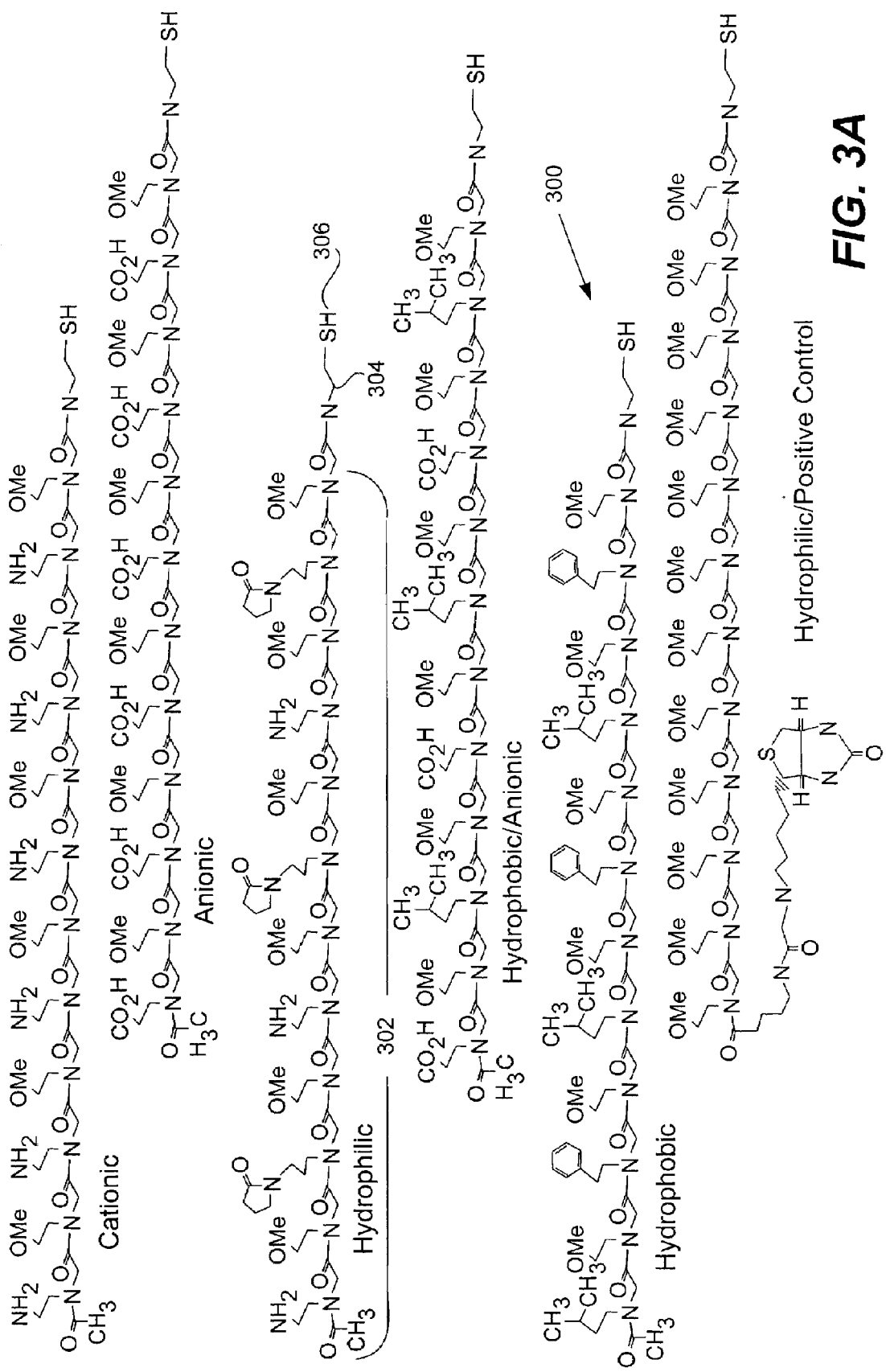
FIG. 3A schematically depicts the molecular structures of six 12-mer peptoid array elements in accordance with one embodiment of the present invention.

FIG. 3A illustrates an example of a small set of array elements 300 wherein the peptidomimetic protein-binding segments 302 are 12-mer peptides, the linker 304 is a short aliphatic chain, and the anchoring group 306 is a thiol. The peptidomimetic segments depicted in FIG. 3A illustrate a subset of the range of affinity properties achievable using peptoids as the peptidomimetic segment, in accordance with one embodiment of the present invention As mentioned above, the number of different types of binding agents present on the surface of the array is at least two. By "different", it is meant that the sequence of monomeric units between two different peptidomimetics of two different protein-binding agents is not the same. While the number of different species of protein-binding agents present on the surface of the array is at least 2, at least about 10, at least about 50, or at least about 100, it is typically much higher, generally being at least about 1,000 usually at least about 5,000 and more usually at least about 10,000. The number may be as high as 500,000 or higher, but typically does not exceed about 100,000 and usually does not exceed about 50,000.

The surface regions surrounding the protein-binding array elements may be modified so as to minimize background non-specific binding of proteins, allowing complex samples (e.g., lysates or serum) to be examined in a single step. The surface may be blocked chemically with hydrophilic termini such as alcohols, carbohydrates, amino acids, sulfoxides, acrylamides, or ethers. Examples of alcohol terminal groups are, for example, mercaptoethanol, mercaptohexanol, mercapto-octanol, in the case of a maleimide-treated surface. These block the unreacted maleimides on the surface. The surface can also be blocked using proteins such as solutions of 1%–10% bovine serum albumin ("BSA") or human serum albumin ("HSA") in phosphate buffered saline, or 1%–10% non-fat dry milk or 1%–10% casein, gelatin or other suitable blocking protein. In some cases, the addition of detergents to the blocking protein solution is advantageous. For example, the addition os 0.01%–0.5% Tween-20 or Triton X-100 (particularly 0.05%), 0.1–2% SDS as are well know in the assay development or surface chemistry arts.

C. General Features of the Array

Typically, the array is characterized by having a plurality of protein-binding agent spots on a solid substrate, where each spot is characterized by having one or more, usually a plurality, of identical binding agents bound to the support surface. The number of distinct spots on the surface of the array may or may not be the same as the number of different protein-binding agents on the array, e.g., the same protein-binding agent may be presented in two or more spots on the array surface. In one embodiment, each protein-binding agent is presented in duplicate in the array. Depending on the nature of the binding agents, the size of the support surface, the methods of fabrication and the intended use of the array, the number of distinct spots on the array surface may vary greatly. Where the support surface has the dimensions of a standard microscope slide (about 3"×1"), the number of spots on the support surface will typically be at least about 3,000, usually at least about 6,000 and more usually at least about 10,000–50,000. The number may be as high as 100,000 or higher, but typically does not exceed about 75,000 and usually does not exceed about 50,000.

The diameter of each spot will typically range from about 100 μm to about 300 μm, usually from about 200 μm to about 300 μm. The space between any two given spots will generally be between about 1 μm and about 50 μm. The density of the spots generally ranges from about 1 to about 5,000 spots/cm$^2$, usually from about 100 to 2,000 spots/cm$^2$. Typically, the spots are arranged across the surface of the spacer layer in the form of a pattern. The pattern may be in the form of organized rows and columns of spots, e.g., a grid of spots, across the substrate surface, a series of curvilinear rows across the substrate surface, e.g., a series of concentric circles or semi-circles of spots, and the like. To further increase density, the spots may also be hexagonally arranged. Still other arrangements of spots are within the scope of the present invention.

2. Methods of Making the Protein-Binding Agent Arrays of the Subject Invention The arrays of the subject invention may be prepared using any convenient protocol. One protocol of interest involves 1) the procurement of a solid support having a surface activated for binding of a protein-binding agent; and 2) contact of two or more different protein-binding agents with the support surface under conditions such that the protein-binding agents become stably associated with the support surface.

A. Solid Support Fabrication

The solid support may be fabricated using any convenient methodology, which methodology will vary depending the particular nature of the solid support. In accordance with one embodiment of the invention a glass support is coated with a layer of metal, e.g., aluminum or gold. To prepare a solid support of glass coated with a metal layer, the surface of the glass is coated with a thin layer of the metal, e.g., gold, silver, platinum, copper, titanium, or aluminum, etc. in a thickness as described above. The metal layer may be deposited on the substrate surface using any convenient protocol, where suitable protocols include e-beam deposition, vapor deposition, sputtering, and the like, and are known to those of skill in the art. See e.g., Moteshari et al., J. Am. Chem. Soc. (1998) 120:1328–1336; Bain et al., J. Am. Chem. Soc. (1989) 111:7155–7164; Lee et al. Langmuir (1998) 14:6419–6423; Folkers et al., Langmuir (1992) 8:1330–1341. Where convenient, an adhesion metal layer may be present between the metal layer and the substrate, where adhesion metals of interest include titanium, chromium, and the like, deposited in a thickness as described above. In addition, oxide overlayers such as silicon dioxide or silicon monoxide may be deposited by e-beam or sputtering deposition on top of the metallic layer.

In one example, following preparation of a gold substrate, if the protein-binding agent's anchoring group is a thiol and the linking group is sufficiently long (as explained above), arrays in accordance with the present invention can be formed by spotting thiol-displaying protein-binding agents onto bare, clean gold. The gold surface of the substrate may be cleaned using a chromic acid cleaning solution (e.g., chromium oxide or sodium dichromate in sulfuric acid, for example Nochromix, available from Fisher (50–80% Sodium dichromate in 12 N sulfuric acid)) and rinsed with HPLC-grade water. This has the advantage of reducing the number of surface functionalization steps.

In another embodiment, where the protein-binding agent's anchoring group is a functionalized modified silane (e.g., mono-, di- or tri-functional silanes, such as chlorosilane, an alkoxysilane, dichloro or dialkoxy silane, or trichloro or trialkoxy silane), the anchoring group can be attached directly to oxide-containing surfaces such as glass, titanium oxide or aluminum oxide. Arrays in accordance with these embodiments of the present invention can be formed by spotting active silane-displaying protein-binding agents onto the oxidized substrate surface. A glass substrate has surface hydroxyls available for this binding. Metal substrate surfaces may be oxidized, for instance by thermal or chemical treatment. For example, aluminum may be oxidized electrochemically, thermally or chemically (e.g., with $H_2O_2$), as is well known in the art. In addition, a silicon dioxide or titanium oxide layer can be deposited on the aluminum. An oxide may also be present as a native thin layer, such as occurs with aluminum or silicon. This native oxide may then be derivatized by the amino-silane.

In still another embodiment of the invention, a metal, e.g., gold or aluminum, substrate surface is first functionalized with functionalized organic molecules that form ordered monolayers. The termini of the organic molecules are functionalized with a reactive group that can attach to a suitable anchoring group of a protein-binding agent. Suitable terminal groups may be, for example, maleimide, hydrazide, aminooxy, an activated ester such as N-hydroxysuccinimide, anhydride, aldehyde, disulfide, thiol, azide, phosphine or avidin, depending upon the anchor's functional group.

In one embodiment the functionalized organic molecules are amino-modified thiol molecules. In order to functionalize the metal surface with the thiol molecules, the substrate having the metal surface may be dipped in a solution of the amino-modified thiol; the amino-modified thiol solution then may be deposited onto the surface of the substrate. Other convenient protocols may be employed. Typically, the gold substrate is immersed into the amino-modified thiol solution under conditions and for a sufficient period for the amino-modified thiol molecules to assemble into a monolayer on the substrate surface. The temperature at which contact is carried out typically ranges from about 10° C. to about 100° C., usually from about 15° C. to about 80° C. Contact is maintained for a sufficient period of time for the self-assembled monolayer to form on the gold surface, where contact is typically maintained for at least about 20 minutes, usually at least about 4 hours, and more usually at least about 16 hours.

Alternatively, the amino thiol can also be deposited by vapor deposition in a vacuum oven or by spin coating. For example, a 1–10% (e.g., 5%) solution of thiol in a volatile solvent such as isopropanol, methanol, THF may be prepared. The slides may be spun at about 1000–8000 rpm (e.g., 5000 rpm) to provide an even deposition of the thiol. Then, a heterobifunctional molecule (e.g., succinimidyl 4-(N-maleimidomethyl)-cyclohexane-1-carboxylate (SMCC) or LC (long-chain)-SMCC) that is an activated ester on one end and a maleimide on the other is contacted with the amino group to create the maleimide-terminated surface. Other heterobifunctional cross-linkers could also be used with different length spacers (e.g., a long ethylene oxide spacer (e.g., 2–4 units) between an NHS ester on one end, and a maleimide on the other end. As noted above, the spacer on the substrate serve the same purpose as and the "linker" in the protein-binding agent.

In another embodiment, Aluminum slides may be used. Aluminum metal may be deposited by e-beam deposition onto a clean glass substrate. The aluminum is then overcoated by silicon dioxide ($SiO_2$) or silicon monoxide in a thickness that is the same or thinner than ¼ the wavelength of the emission or excitation light. Oxide thicknesses of about 600 to 1000 Angstroms may be used as these eliminate the need for thinning the oxide prior to performing binding experiments. The aluminum/oxide surface may be treated with a amino-modified silane. For example, aluminum slides freshly coated with a 800–1,400 Angstrom layer of silicon dioxide, may be dipped immediately into a bath of 3%–40% aminopropyl triethoxysilane in isopropanol, that has been previously filtered through an 0.2 uM filter membrane, and silanized for up to 1 hour, followed by rinsing and drying. Alternatively, aluminum slides coated with silane (APS) are available from Amersham-Pharmacia, Amersham, England (and described in International Patent Application No. WO 98/53304). In some cases, such commercially available slides may require thinning of the oxide layer to between about 200 Å and about 1,000 Å, more particularly between about 900 Å and about 1,000 Å, prior to performing a binding experiment to improve signal-to-noise ratios. The final amino-modified Al surfaces may be functionalized with SMCC to render a surface that presents maleimide functional groups. Here again, the silane may also be vapor deposited or spin coated, as described above. For example, a 1–10% (e.g., 5%) solution of silane in a volatile solvent such as isopropanol, methanol, THF may be prepared. The slides may be spun at 1,000–8,000 rpm (e.g., 5,000 rpm) to provide an even deposition of the silane. Then, a heterobifunctional molecule (e.g., succinimidyl 4-(N-maleimidomethyl)-cyclohexane-1-carboxylate (SMCC or LC-SMCC)) that is an activated ester on one end and a maleimide on the other is contacted with the amino group to create the maleimide-terminated surface. Other heterobifunctional cross-linkers could also be used with different length spacers (e.g., a long ethylene oxide spacer (e.g., 2–4 units) between an NHS ester on one end, and a biotin or maleimide on the other end. As noted above, the spacer on the substrate serve the same purpose as and the "linker" in the protein-binding agent.

Further in accordance with this embodiment, it has been found that amplification of the fluorescent signal used in assays conducted with microarrays in accordance with the present invention may be enhanced by etching the commercially available functionalized and spotted aluminum slides (Amersham) to reduce the oxide layer thickness to about 200 Å to about 900 Å, preferably about 500 Å. For example, an etch solution of about 0.1–0.2% SDS/5×SSC (0.75 M NaCl/0.085 M sodium citrate) and optionally 5 mM EDTA may be applied at about 50–80 degrees, preferably about 60° C. for about two to four hours. As noted above, manual deposition of a silicon dioxide layer of a suitable thickness may eliminate the need for the thinning of the slide.

As noted above, where the substrate surface has an organic self-assembled monolayer, following self assembly of the initial monolayer, one or more additional monolayers may be grafted onto the initial monolayer, where the additional layer(s) are made up of molecules, e.g. alkyls, having functionalities that provide for their covalent attachment to the surface functionalities of the initially deposited monolayer, e.g. amino functionalities where the initially deposited monolayer is characterized by the presence of carboxy functionalities. Alternatively, multi-component spacers can be constructed prior to attachment to the surface.

B. Synthesis of the Protein-Binding Agents

As noted above, protein-binding agents in accordance with the present invention are composed of three segments: a peptidomimetic, an anchor, and a linker connecting the peptidomimetic and the anchor.

Peptidomimetics may have a variety of nonpeptide polymeric structures and characteristics as long as they can mimic the biological effects of natural peptides. References to peptidomimetic structures have been provided above. In one embodiment of the present invention, the peptidomimetic segment of the protein-binding agent is a peptoid.

Figure 2:
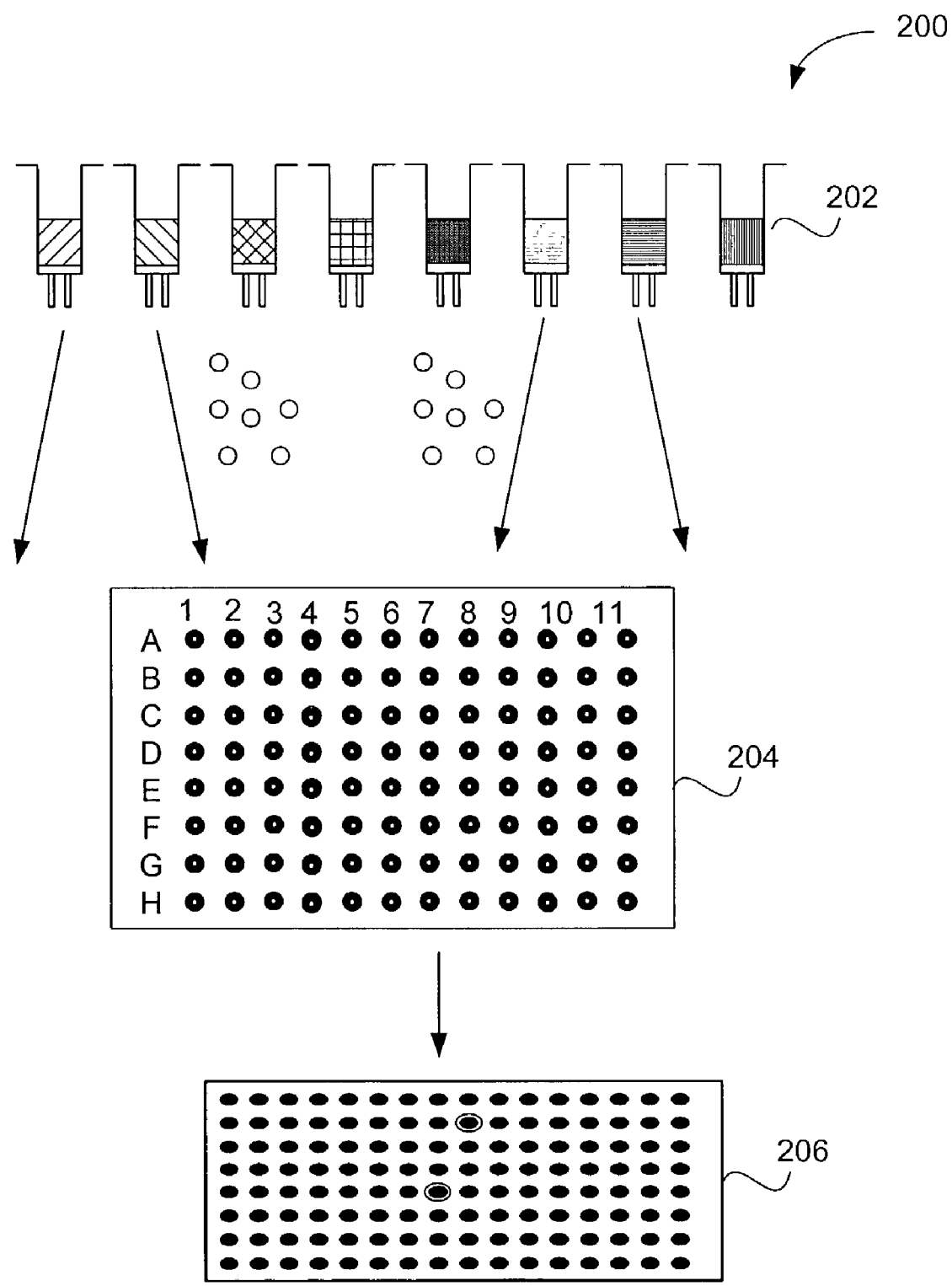
FIG. 2 schematically depicts a process of making an array having a plurality of different protein-binding agents stably associated with the surface of a solid support in accordance with one embodiment of the present invention.

Libraries of peptoids may be synthesized using robotic solid-phase synthesis techniques, such as those developed by Chiron Corporation of Emeryville, Calif. The diversity of the library can be controlled by the nature and arrangement of the amine submonomers (bromoacetic acid and substituted amines) used in the peptoid synthesis, as described in above-incorporated U.S. patent documents. As illustrated in FIG. 2, libraries may be prepared according to a process 200 using mix and split synthesis 202, or parallel synthesis, such that there is a multiplicity of peptoids synthesized, but only one species of peptoid on a given bead (i.e., each bead has one unique compound, repeated many times). The amount of compound per bead may range from about 1–100 nanomoles, with 20–40 nanomoles being most typical. About 40 nanomoles per bead are commonly obtained. This process is further described in U.S. patent application Ser. No. 09/306,700, the disclosure of which is incorporated by reference herein in its entirety and for all purposes. The synthesized peptoids, still bound to resin, may then be distributed to 96-well plates (or other multi-well plates, such as 384-well or 1024-well plates) 204 using, for example, bead picking technology described in the just-referenced U.S. Patent application. The use of 'big bead' resin (having a diameter of about 500μ) allows distribution of one bead per well.

The peptoids may then be then dried, cleaved from the resin (e.g., with about 20–95% TFA in dichloromethane; 95% being typical), re-dissolved in acetonitrile/water, filtered or centrifuged, dried and re-dissolved in 50% DMSO/50% Buffer. Other solvent/buffer systems can also be used such as 50% DMF or 50% NMP with the remainder being PBS, TBS, Borate, Tris-HCl, etc. In some cases, a reducing agent such as tris-carboxyethylphosphine (TCEP) may also be added to the wells of the spotting plate to inhibit oxidation of the thiols on the peptoids so that they retain their reactivity toward maleimides on the substrate surface. In cases where TCEP is added to the wells, phosphate buffers such as PBS are to be avoided, and buffers such as TBS would be preferred. This final solution is ready for spotting.

In one embodiment of the present invention, the concentration of peptoids in the wells of the spotting plate should be in the range of about 0.5–2 mM, where 2 mM is preferred. For spotting onto the prepared planar solid support 206, the peptoids are filtered or centrifuged, dried, and resuspended, as described in further detail below. It is useful for the material spotted on the slide be in an excess with respect to the amount of probe in solution to be applied to the microarray. This is an amount that gives a saturating fluorescence signal, so that changes in signal intensity are due substantially to protein levels.

The anchoring and linker groups may be attached to the peptoid at either the C- or N-terminus. They can be attached either as a submonomer (e.g., as described in U.S. Pat. No. 5,877,278 and above-referenced co-pending U.S. patent application Ser. No. 60/282,115) during the peptoid synthesis as described above in the patent documents incorporated by reference, or with in situ activated amino acid coupling steps, as a modification of the peptoid after synthesis, according to procedures known to those of skill in the art.

For N-terminal attachment, the peptoid may be synthesized on a resin and then the linker and the anchor groups may be added before the entire molecule is cleaved. For example, peptoids may be prepared on Rink amide polystyrene resin as illustrated and described in co-pending application Ser. No. 09/704,422 previously incorporated by reference herein. The synthesis procedure is also reported in Figliozzi, G. M., Goldsmith, R., Ng, S. C., Banville, S. C., Zuckermann, R. N. *Methods Enzymol.* 1996, 267:437–447, the disclosure of which is incorporated by reference herein for all purposes. Also, before cleavage, one or more (e.g., two to four, preferably four) submonomer hydrophilic linker groups (e.g., methoxyethylamine) may be added to the peptoid N-terminus. Then, a trityl-protected cysteamine is added in order to provide a thiol anchoring group. The peptoid with attached linker and anchoring groups may then be cleaved from the resin, for example using 95% TFA (v/v) in dichloromethane ($CH_2Cl_2$). The resulting solution is then ready for application (spotting) onto microarray slides in accordance with the present invention.

In another embodiment, an FMOC-protected beta-alanine is attached to the N-terminus of the peptoid by in situ activation with Hobt and DIC, as is known to those skilled in the arts of peptide synthesis. The beta alanine functions as an adaptor molecule between the peptoid and peptide linker. After attachment of beta-alanine, an FMOC-protected amino acid on a peptide (e.g., glycolic) linker, for example, is attached to the N-terminus of the beta-alanine. Finally, biotin is added to the N-terminus by peptide coupling.

The thiol or biotin anchoring group can also be attached to the end of the peptoid at the C-terminus. For example, 4-(diphenylhydroxymethyl)benzoic acid (available from Fluka) is treated with cystamine hydrochloride in the presence of an acid catalyst. Next the resulting amine is protected as the N-(9-flurenylmethoxycarbonyl) (N-FMOC) derivative, and the resulting FMOC-NH—$CH_2CH_2$—S-Tr-COOH is coupled to aminomethyl-Big Beads (400–500 microns, Polymer Labs). The peptoid is synthesized on the deprotected amine as described above, and treatment with TFA results in cleavage of the thiol-modified peptoid from the resin, while leaving the trityl protecting group on the resin. Such procedures are described in the above-referenced co-pending U.S. patent application Ser. No. 60/282,115

C. Contacting the Solid Support with Protein-Binding Agents

Following preparation of the substrate and protein-binding agents, as described above, two or more different protein-binding agents of interest that are to be bound to the surface to produce the array are contacted with the functionalized, or otherwise prepared (cleaned, oxidized, etc.) substrate surface. By contact is meant that the binding agents are brought into proximity with the surface such that they become substantially stably attached or bound to the surface of the substrate layer.

In contacting the binding agents with the substrate surface, any convenient means for contacting the surface with the binding agents which results in the desired pattern of binding agent spots, as described above, may be employed ,e.g., by spotting. As mentioned above, the term contact is used herein to refer to any method that brings the binding agent within close proximity of the support surface. Generally, an aqueous solution (e.g. water, water/organic solvent (such as 50/50 water/DMSO, or the like) of the binding agent is employed during contact where the solution may comprise one or more components in addition to water and the binding agent, e.g., buffering agents, salts, and the like. Other systems include 50/50 NMP/TBS, DMF/TBS, NMP/PBS, DMF/PBS, or all these solvents together with water. The 50/50 mix can also be adjusted. For example, when a higher percentage of the aqueous solution is used, the drop sizes can be smaller because of the higher surface tension of the solution. Drop size (and therefore density) may be controlled to some extent in this manner. Typically, contact is achieved by depositing solutions of the different binding agents onto discrete locations of the support surface, such that each different type of binding agent is deposited onto its own unique location on the substrate surface.

The binding agents may be deposited onto the support surface using any convenient means, e.g., by pipetting. A number of devices and protocols have been developed for depositing aqueous solutions onto precise locations of a support surface and may be employed in the present methods. Such devices include "ink-jet" printing devices, mechanical deposition or pipetting devices and the like. See e.g., U.S. Pat. Nos. 4,877,745; 5,338,688; 5,474,796; 5,449,754; 5,658,802; 5,700,637; and 5,807,552; the disclosures of which are herein incorporated by reference. Robotic devices for precisely depositing aqueous volumes onto discrete locations of a support surface, i.e., arrayers, are also commercially available from a number of vendors, including: Genetic Microsystems; Molecular Dynamics; Cartesian Technologies; Beecher Instruments; Genomic Solutions; and BioRobotics. Alternatively, bubble jet technology recently described by Okamoto, Suzuki and Yamamoto, *Nature Biotechnology,* vol. 18 (April, 2000), 438, may be used.

As noted above, an important feature of a process in accordance with the present invention is that the reaction between the anchoring group on the protein-binding agent and the substrate surface must be sufficiently facile so that it is complete within the average lifetime of a droplet that is deposited by the robotic array spotter onto the surface. For example, if the surface is functionalized and displays a maleimide, a suitable anchoring group is a thiol and approximately 15–20 minutes at about 60% humidity are required for completion of the binding reaction. As noted above, other surface display/anchor combinations are possible, including those forming stable, yet non-covalent bonds, such as avidin and biotin.

D. Blocking the Chip

After spotting of the peptoid library onto the array substrate (chip), the remaining, uncoated surface of the chip may be functionalized with a molecule that displays a hydrophilic terminus. These hydrophilic termini are anticipated to reduce or eliminate non-specific binding of proteins in the complex mixture. The hydrophilic portion may consist of alcohols, sulfoxide, carbohydrates, acrylamides, with hydrophilic termini such as alcohols, carbohydrates, amino acids, sulfoxides, acrylamides, and ethers or other low-protein binding group. The hydrophilic display molecule is anchored to the chip in the same manner as the peptoid that has already been spotted. For example, chips spotted with the peptoid library may be chemically blocked with cysteine, mercaptoethanol or other suitable hydrophilic thiol. The chips may also or alternatively be blocked with protein such as 2% BSA/PBS, 10% non-fat dry milk or 1% casein for at least 1 hour, rinsed with water and dried. Other possible blocking agents are noted above. The blocking agents may be applied to the chips in ways well known to those of skill in the art, such as by dipping the chips in a solution of a blocking agent, by painting the surface of the chips with a blocking agent solution, or by spin-coating.

Alternatively, the surface regions surrounding the array elements may be modified with polymeric or oligomeric chemical blocking agents so as to minimize background non-specific binding of proteins, allowing complex samples (e.g., lysates or serum) to be examined in a single step. The surface may be blocked chemically following spotting of the array elements with a hydrophilic polymeric or oligomeric molecule that reduces or eliminates non-specific protein binding to the array. As opposed to conventional protein blockers such as BSA and casein, the polymeric or oligomeric chemical blocker is a synthetic molecule that may be used alone or together with a protein blocker. In a specific embodiment, a chemical blocker and a protein blocker may be used together, e.g., chemical block followed by protein block in sequence or chemical block mixed with protein block and then applied to the array surface after spotting. The polymeric or oligomeric chemical blocking agent may be attached to the array by dipping the slide into the blocking agent after spotting.

For example, in a specific embodiment, the chemical blocking agent is a polyethylene glycol (PEG) analog, modified at at least one terminus so that it will react with and bind to the organic functionalized substrate surface not occupied by array elements. For example, the chemical blocking agent for a maleimide functionalized surface may be a thiol-modified polyethylene glycol (PEG). One specific example is a dithiol-modified PEG (SH-PEG-SH), for example having a molecular weight of about 3400–5000 (for example, commercially available from Shearwater Polymers). The blocking agent may be applied with casein after the array element spotting is completed, as described below, or in a step beforehand. The possible functionalities for the blocker termini are the same as those for the adapters noted above, e.g., could be biotin, amine, activated ester, etc.

Another type of chemical blocking in accordance with the present invention is provided by well-defined, monodisperse oligomers of N-substituted glycines (peptoids) derivatized with hydrophilic side chains that can be readily attached to a variety of surface functionalities. Suitable side chains may have one or more ethylene glycol units, or may also be composed of hydroxyls, sulfoxides, or other hydrophilic groups (such as described above) that resist protein adsorption. These molecules are designed to resist protein binding and would be interspersed with the specific protein binding molecules of the protein array (e.g., antibodies, fusion proteins, etc). These chemical blockers may be optimal for high density packing of the protein-resistant moieties and thus provide improved resistance to non-specific protein binding (NSPB).

These chemical blocker oligomers may be prepared using the submonomer peptoid synthesis method described above. For a peptoid-based chemical blocking agent, suitable N-substitutions are moieties that are known to be highly resistant to non-specific protein binding, such as ethylene oxide, sulfoxide, hydroxyl, etc. The N-terminus can be modified with a variety of surface immobilization groups such as biotin, thiol, hydrazide, aldehyde, epoxide, triethoxysilane, etc., as previously described.

The length of the peptoid blocker can be readily varied from about 2–100, where 15–30 is practical and would result in pure materials without a subsequent purification step. The length of the side chains can be varied from between 1–10, with 1–5 providing facile coupling to the peptoid backbone. In addition, both the C-terminus and N-terminus may be modified with a variety of chemical ligation reagents. Molecular weights can be in the range of 500–5000, generally around 2000–3000.

After synthesis has completed, the peptoid may be cleaved using conventional cleavage reagents such as 95% TFA/5% water. This method can yield NSPB-peptoids in multi-gram quantities which can readily be used to coat microarray slides in fairly large batches (e.g., 20 slides at a time, using 200 mL of coating solution). In the course of a microarray binding experiment, the NSPB-peptoid may be incorporated directly into a protein blocking solution such as casein, non-fat milk, BSA, etc. Alternatively, it may be used as a separate coating step before or after protein blocking. The mode of attachment of the microarray element (e.g., peptoids) to the surface would likely determine the motif of NSPB-peptoid used. For example, if biotinylated proteins are attached via robotic spotting to avidin-coated slides, then a biotinylated NSPB-peptoid would be used as the coating to block NSPB.

FIG. 3B illustrates a peptoid-based chemical blocking agent in accordance with the present invention. The peptoid-based polymer or oligomers chemical blocker is designed to stay hydrated and resist the nonspecific binding of proteins. In the figure, $R^1$=H or Me, m=2 to 100, n=1 to 10.

E. Summary

FIGS. 4A and 4B briefly illustrate processes for making protein-binding agent arrays for some embodiments of the invention in accordance with the procedures described above. In FIG. 4A, a process (400) for making an array in which protein-binding agents are bound directly to the inorganic surface of a bare planar substrate is depicted. A planar substrate 412 with a gold or aluminum surface is provided (410). The surface is prepared for binding (cleaned) as described above. Protein-binding agents 422 with a thiol anchoring group 434 are spotted onto the substrate 412 (420). Once binding of the protein-binding agents is complete, a blocking agent 432, namely a hydrophilic group, such as an alcohol, or a protein is applied to the surface of the substrate 412 where no protein-binding agent 422 is bound (430).

In FIG. 4B, a process (450) for making an array in which protein-binding agents are bound to the surface of a planar substrate via an organic surface layer is depicted. A planar substrate 462 with a gold or aluminum surface is provided (460). The surface is prepared for binding by applying a functionalized amino-modified thiol or amino modified silane layer 464, as described above. The layer 464 includes a thiol or silane functionality 466 which binds to the gold or aluminum surface of the substrate 462 and a binding functionality 468, such as maleimide, for a subsequently bound protein-binding agent. Protein-binding agents 472 with anchor group functionality 474 complementary to the substrate surface layer binding functionality 468 are spotted onto the substrate (470). Once binding of the protein-binding agents is complete, a blocking agent 482, namely a hydrophilic group, such as an alcohol, or a protein is applied to the surface of the substrate where no protein-binding agent 472 is bound (480).

3. Methods of Using the Protein-Binding Agent Arrays of the Subject Invention

The subject arrays find use in a variety of different applications in which binding events between the surface bound binding agents of the array and analyte(s) of interest in a test sample are detected. In other words, the arrays of the subject invention find use in binding assays. In such applications, the support bound binding agent generally acts as a "target" for the analyte "probe" in the test sample. The analyte probe is typically labeled, e.g., where the label may be a directly detectable label (e.g., radioactive isotope, fluorescent label, chemiluminescent label, etc.) or an indirectly detectable label (e.g., member of a signal producing system, such as a ligand for a labeled antibody, where the label may be enzymatic which converts a substrate to a chromogenic product, etc., where the labeled antibody may be a secondary labeled antibody) so that binding events may be readily detected.

In particular, arrays in accordance with the present invention are useful in performing proteomic analyses of complex protein samples. As used herein, proteomics is the separation and/or quantitation and/or identification of one or more proteins in a sample. The sample may be derived from a cell (e.g., the cell's cytosol, membrane or extra-cellular proteins), tissues (e.g., dissected or laser-microdissected), body fluids (such as urine, blood spinal fluid) or any other sample containing proteins. The results of such separation/quantitation/identification may produce novel protein targets for drug screening, proteins for diagnostics, or novel synthetic ligands for assays or protein purification. The arrays may very effectively be used in differential protein binding assays. For example, two (or more)-color fluorescent labeling of complex protein mixtures, and the analysis of differential protein binding to the array by fluorescence imaging may be conducted. As described below, the arrays may be used in conjunction with other techniques to identify, sequence and structurally characterize differentially expressed proteins or peptides of interest. The arrays may be run in parallel with DNA arrays and the differential binding results compared to identify correlations between gene activity and protein expression. Also, mixed arrays, wherein the molecules making up an array includes antibodies, etc. may be prepared and used to conduct binding assays.

A variety of techniques can be used to conduct differential binding assays using arrays in accordance with the present invention ("proteomic microarrays"). Some of these techniques, as used in embodiments of the present invention, are described below:

A. Protein Labeling

Complex protein samples are labeled using standard techniques, many of which have been developed for 2-D gel analysis of protein mixtures. For example, sample A may be labeled with an amine reactive Cyanine 3 dye ("Cy 3") ($\lambda_{ex}$=550 nm/$\lambda_{em}$=570 nm), and sample B is labeled with an amine reactive Cyanine 5 dye (Cy 5) ($\lambda_{ex}$=650/$\lambda_{em}$=670 nm) (dye reagents available from Amersham-Pharmacia). Samples A and B may be, for example, from normal or diseased, treated or untreated, etc., tissues or cell lines, respectively. The unreacted dye may be separated from the labeled protein using standard methods such as gel filtration, dialysis, etc. Of course, as noted above, a variety of different labels, as are well known to those of skill in the art, including, but not limited to, tetramethylrhodamine-isothiocyanate (TRITC), fluorescein-isothiocyanate (FITC), and succidimidyl ester derivatives, thereof, or any other dye molecule that may be reacted to proteins via amino acid side chains such as amine side chains (lysine), thiol side chains (cysteine) or other suitable functional group.

B. Binding Assay and Chip Readout

Labeled protein samples are incubated with the proteomic microarray chip for periods of time, and under a variety of conditions of pH, salt content and temperature anticipated to modulate the affinity of various proteins to the elements of the array. Generally, the samples are contacted with the microarray by introduction of an appropriate volume of the fluid sample onto the array surface, where introduction can be flooding the surface with the sample, deposition of the sample onto the surface, e.g., with a pipette, immersion of the entire array in the sample, and the like. In many embodiments, the solution is deposited onto the surface and then sandwiched beneath a cover slip or in a sealed chamber.

For example, a 25 μL–100 μL (typically 50 μL) aliquot of each probe solution may be applied to the surface of a typical microscope slide-sized chip, and a cleaned coverslip placed on top, forming a sandwich of the probe solution on the chip surface. The protein solutions may then be co-incubated with the chip for at least 1 hour, or overnight. After incubation, the coverslip is removed and the chip is washed, for example, in 1×PBS/0.05% Tween or other suitable buffer containing surfactant. The chip may be washed using a variety of conditions that decrease or increase stringency. These conditions can again be customized to allow, for example, retention of only the most strongly bound proteins. Or, as the case may warrant, less stringent washing may be used to allow visualization of comparatively weaker bound proteins. The choice is likely to be determined by the complexity and diversity of the peptidomimetic (e.g., peptoid) array that is displayed on the chip and the nature of the protein mixture. The washed chips are then dried, for example, under a stream of Argon or Nitrogen.

After suitable washing, the chip is read in an array scanner, such as are well known in the art. The ratio of Cy 3 to Cy 5 for each spot is determined using commercially available software. Spots that show a ratio considerably greater than or less than one are observed, and deemed to be "differential".

Figure 5:
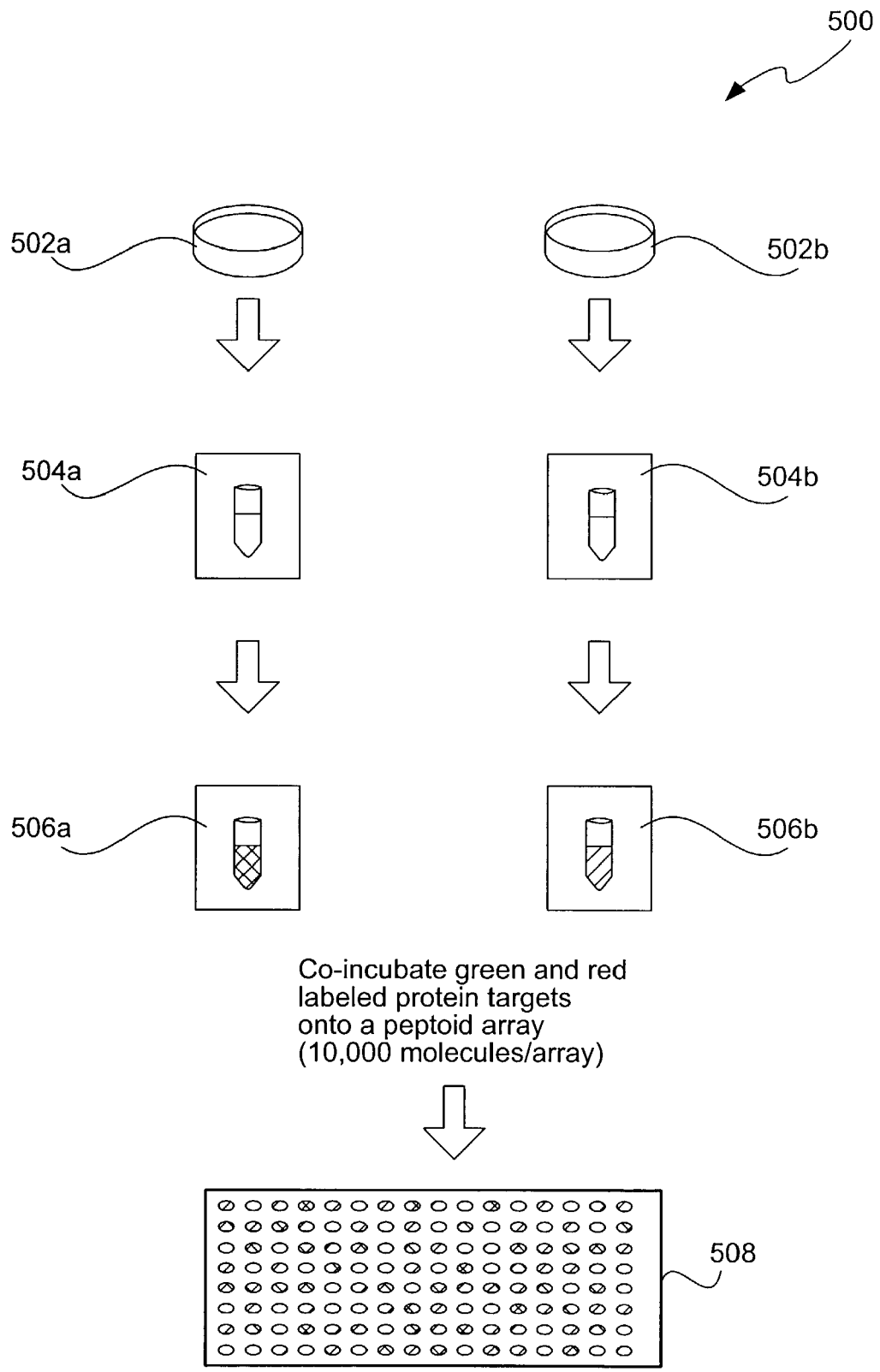
FIG. 5 schematically depicts a process for conducting a differential protein binding assay in accordance with one embodiment of the present invention.

FIG. 5 briefly illustrates a process for conducting a differential proteomic binding assay using protein-binding agent arrays for one embodiment of the invention in accordance with the procedures described above. In FIG. 5, the process (500) begins with the procurement of two biological samples to compare, e.g., an "untreated" cell line 502a and a "treated" cell line 502b. Cell lysates 504a,b are isolated from the cell line samples. The lysates are labeled, for example, the "untreated" cell lysate 504a is labeled with a fluorescent green dye while the "treated" cell lysate 504b is labeled with a fluorescent red dye. The labeled samples 506a,b are then co-incubated on a protein-binding array chip 508 in accordance with the present invention, e.g., an array of peptoids. The protein in the samples can either be denatured or native. For example with the addition of 1–2% SDS the proteins in the samples may be denatured and clusters or hydrophobic interactions minimized or eliminated. Alternatively, the clusters, which may be important in elucidating protein-protein binding pathways, and proteins may be kept in their native states and the results studied. The chip is then read in a array scanner.

C. Library Sequencing

The sequence of the peptidomimetic that binds a differentially expressed protein may be determined by library sequencing techniques. This can be achieved, for example, by MS/MS methods that allow fragmentation of the peptoid along the amide backbone. These methods are described in co-pending U.S. patent application Ser. No. 09/580,380, the disclosure of which is incorporated herein by reference for all purposes (see also PCT Publication No. WO 00/72004). From the mass of the fragmentation product, the structure and sequence of the isolated peptoid can be determined.

D. Post-Array Processing: Protein Isolation, Purification and Identification

Once a protein or set of proteins is determined to be differential between samples A and B, it can be isolated by preparing chromatographic supports composed of the same peptidomimetic (e.g., peptoid) identified on the chip. Peptoid-based chromatographic supports, their preparation and their use are described in U.S. patent application Ser. No. 09/704,422, previously incorporated by reference herein.

In accordance with one embodiment of that disclosure, a peptoid sequence that produces a differential on the chip may be synthesized on hydrophilic resins that are hydrophobically "masked" during peptoid synthesis. After synthesis, the resin in "unmasked" to reveal hydrophilic groups compatible with biological solutions. Such a resin is immediately available for protein binding/isolation experiments.

Once the protein is isolated, it's sequence can be determined using standard techniques such as MALDI/TOF mass spectrometry or trypsin digests.

Figure 6:
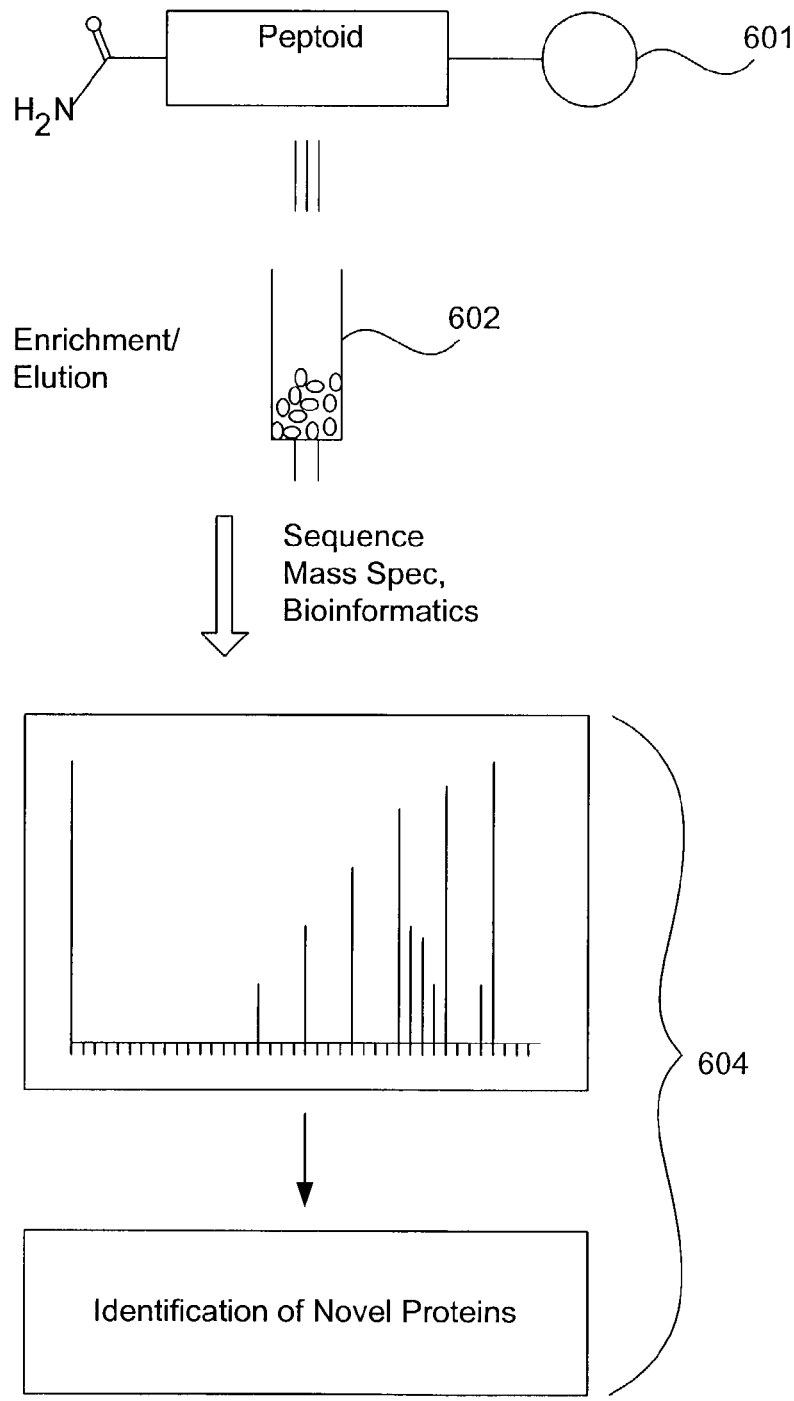
FIG. 6 schematically depicts a various processes for identifying and characterizing proteins identified in accordance with embodiments of the present invention.

FIG. 6 briefly illustrates aspects of post-array processing in accordance with the procedures described above and below. In FIG. 6, the process (600) begins with the preparation of chromatographic separation columns 602 using peptidomimetic agents 601, e.g., peptoids, identified as of interest in a proteomic differential binding assay conducted using a proteomic microarray in accordance with the present invention. An aliquot of the complex sample originally run on the microarray is then run through the column. The protein of interest preferentially binds to the column and is thereby separated form other components of the sample. The bound protein is eluted and may then be used in further analyses 604, such as protein sequencing, tertiary structure determination, etc. In addition, data relating to the identification of the protein may be entered into bioinformatics databases for further research.

Alternatively, the same peptoid that bound the differentially expressed protein could be spotted repetitively on a chip and incubated with the an aliquot of the same lysate. The same protein should bind to the array, but in a much larger area than just the one spot on the original chip. Laser desorption mass spectrometry can then be used to sequence the protein directly from the chip.

E. Other Applications

The anticipated uses of proteomic microarray chips in accordance with the present invention are broad. In general, the applications have in common the identification of a protein or set of proteins that are over-expressed or under-expressed in one complex mixture relative to another (or present/absent, such as in the case of a diagnostic protein). Those skilled in the art will recognize that embodiments of the present invention are compatible with a wide variety of assay formats including sandwich assay, such as ELISA.

As described above, proteomic microarrays may be used to determine differential expression of proteins in complex solutions by alternatively labeling (e.g., Cy 3 for one sample and Cy 5 for another) the two or more protein solutions to be compared. The chips may be used to find novel protein targets for later high throughput screening assays. In another particularly powerful application, the methodology may be used to purify a recombinant protein that is overexpressed in a particular host such as yeast or baculovirus. The sample that contains the expressed protein is compared to the sample that does not by co-binding the alternatively labeled samples on the chip, and looking for differentials. The procedure identifies peptoids on the array that bind with reasonable affinity and specificity to the expressed protein. These same peptoids are then used for generating chromatographic resins for the isolation and purification of the recombinant protein of interest.

In an analogous manner, the proteomic microarry chips may be used to find protein markers in plasma or serum that may be diagnostic of particular disease states such as cancer, HIV, or diabetes, or to find novel targets for drug screening. Also, once a set of ligands has been identified for particular groups of proteins, it is possible to monitor the expression levels of these proteins to decipher mechanisms of drug action. In that regard, the new ligands may be used as probes of protein abundance, analogous to the ways in which antibodies are currently used to determine protein abundance. In addition, by examining the proteins from virulent and non-virulent strains of bacteria or viruses, one can determine unique virulence factors that result in infectious disease. Once these virulence factors are identified, these proteins can be used as targets for screening new anti-bacterial or anti-viral drugs. Alternatively, the chips provided by the present invention may also be used to discover a variety of peptide, antigen, or protein mimetics. For example, novel mimetic cellular adhesion molecules, mimetic drug candidates, or protein mimetics that may be used as chromatographic supports. In addition, the material spotted on the chip could itself be potential drug candidates or function as an initial scaffold for designing new drug candidates. In such embodiments, high throughput assays to identify potential therapeutic agents can be done directly on the chip.

In one embodiment, the proteomic microarrays of the invention are run in parallel with DNA arrays, and the differential binding results derived from each are compared to identify correlations in gene activity and protein expression. For example, differential binding assays are conducted for complex biological samples on both proteomic and DNA arrays. Separate aliquots from the samples are labeled and contacted with a proteomic microarray in accordance with the present invention and a DNA microarray, such as are well known in the art. The differential protein expression evidenced by the binding results on the proteomic array when compared with those for the DNA array may elucidate relationships between protein expression and gene families whose activation is required for that expression.

In another embodiment of the present invention, a "mixed array" chip of the present invention is provided. Peptoid or other peptidomimetic binding elements attached to the chip surface may be mixed with antibody or protein binding elements such that both types of binding elements are present on the same chip. The antibodies can serve as positive controls, or as a means of monitoring the levels of specific proteins in the mixture being analyzed. The peptoids would provide data on differentials in unknown proteins, whereas antibody spots on the chip would provide data on differential levels of known proteins. For example, if a cell is treated with a certain drug, the protein levels might change up or down. If those proteins have known antibodies, it is possible to monitor the change of these with antibody differentials, while at the same time, look for changes in unknown proteins, with the peptoid differentials.

In one example of this technique, antibody solutions are prepared in the same microtiter plates as the peptoid solutions, but in different wells. The peptoids are already functionalized with thiol anchoring groups. The antibodies are reacted with a reducing agent to reduce the disulfide bonds in the antibody hinge and Fc region (for example, as described in Levison, M. E., et al, (1969), Experentia, vol 25, 126–127 and Blauenstein, P., et al, (1995), Eur. J. Nuclear Med., vol 22, 690–698), thus producing a thiol on the antibody. This allows for spotting of both peptoid and antibody in the same spotting session, thereby creating a "mixed" chip. Alternatively, the antibodies may be bound to immobilized Protein A or Protein G on chip surfaces, while peptoids are attached to avidin or streptavidin, presenting a mixed surface for display. Or, antibodies may simply be biotinylated and spotted together with biotinylated peptoids or peptides onto avidin-coated chips.

Another technique that may be combined with the proteomic microarray techniques of the present invention is the MS/MS macromolecular structural analysis technique described in above-referenced U.S. patent application Ser. No. 09/580,380, previously incorporated by reference herein. In this way, the combination of techniques can be used to identify a protein of interest, enrich and isolate it, sequence the protein, and elucidate aspects of its tertiary protein structure.

Data relating to the identification and post-array processing of proteins of interest may also be entered into bioinfomatics databases. The data may be correlated with other biological data therein for further research.

4. Kits

Also provided by the subject invention are kits for performing proteomic binding assays using the subject arrays. Such kits according to the present invention will at least include an array according to the invention. The kits may be configured for analytical or diagnostic purposes, and may further include one or more additional reagents employed in the method for which the array is intended. For example, the kit may include various receptacles, labels, buffer solutions, tools and any other material necessary to conduct a proteomic binding assay. Kits in accordance with the present invention may also be configured to receive samples for analysis and thereafter perform the steps necessary for a binding assay in accordance with the invention without further user manipulation.

EXAMPLES

The following examples provide details concerning the synthesis and characteristics of the proteomic arrays in accordance with the present invention, their components, and applications. It should be understood the following is representative only, and that the invention is not limited by the detail set forth in these examples.

Example 1

Preparation of Microtiter Plates Containing One Compound Per Well

Preparation of one (1) 96-well plate containing 96 single compounds (0.8 mM) in a 1:1 DMSO/PBS solution: A siliconized vial (8 ml, 2 dram) was loaded with a one compound/bead library synthesized on Rink polystyrene macro-bead solid support (66 mg,~1320 beads, 40 nanomole/bead, 0.75 mmol/g, 425–500 um, Polymer Laboratories) that contains a total of 121 possible compounds. The beads were swollen in dichloroethane (DCE, 4 ml) for 24 hours and sieved over stainless steel mesh (600 µm). Using the resulting dichloroethane bead slurry, 96 beads were individually picked and relocated into a polypropylene 96-well plate (200 µL, conical bottom) in order to obtain one bead per well over 96 wells. The resulting 96-well plate, (the 'grandmother' plate), was transferred to a speed-vac evaporator Savant AES200 equipped with a 96-well plate carrier rotor and the remaining DCE was removed from the plate. A cleavage cocktail (TFA/TES/H2O/DCE, 46:2:2:50, 75 µL) was then added to each bead containing well in the plate. After an hour the plate was transferred to the speed-vac evaporator to remove most of the volatiles from the plate. Each well was treated with acetonitrile ($CH_3CN$, 10 µL) and agitated for 10 min using a microtiter plate shaker. The plate was transferred to a speed-vac evaporator and the remaining volatiles were removed from the plate for 10 minutes. Every single compound in each well was dissolved in dimethylsulfoxide (DMSO, 25 µL) and relocated in a 96-well filter plate made of polystyrene, equipped with a polypropylene membrane (0.45 µm). The 96-well filter plate was stacked over a polypropylene 96-well plate (200 µL, conical bottom) and the assembly was transferred to a Beckman GS-6R centrifuge programmed for 5 minutes at 3000 RPM (~2000 G) at 15° C.

This procedure provided the 'mother' plate composed of filtered 96 DMSO solutions (1.6 mM) of one compound in 96 wells. To form the 'daughter plate' (used for spotting), an aliquot of every DMSO solution (5 µL) was transferred to a polypropylene 96-well plate (200 µL, conical bottom). Then, every well in the daughter plate was mixed with degassed solution PBS (5 µL) and stored at −20° C. Alternatively, each compound in each well may be dissolved in 20 µL of 50% DMSO/water. In the case of a plate with a conical bottom, the plate may be centrifuged at 1,800 rpm for 5 minutes to immobilize the bead at the bottom of the conical well, followed by relocation of 10 uL of the clear supernatant into a daughter plate that is ready for spotting.

The same can be done for 384 beads in 384 well plates, or 1,024 beads in 1,024-well plates, etc. For spotting, any suitable spotting device can be used, such as a Molecular Dynamics Generation II (for 96-well) or Generation III (384-well) spotters.

Example 2

Functionalization of Solid Supports for Spotting

Gold or aluminum reflective microscope slides were used as substrates for spotting a library of peptoids. In one example, the peptoid is functionalized with a thiol endgroup and the surface is functionalized with a maleimide. Upon spotting, the thiol on the peptoid reacts with the maleimide on the surface to form a covalent thioether attachment. Gold surfaces activated with maleimide were prepared as follows: 1) Gold-coated microscope slides (1200 Angstroms Au, 30–50 Angstroms Ti or Cr) were cleaned with Chromic acid cleaning solution for 15 minutes and rinsed with HPLC grade water. 2) Gold slides were dipped into 1–5 mM amino-modified thiol (1-Mercaptoundecyldiethoxyamine; a C-11 alkyl, two ethylene oxides, and an amine; alternatively, C-2 to C-20 alkyl groups and/or ethoxy or triethoxy groups could be used in such a compound) for 1–24 hours at room temperature or at 45 or 60° C. The slides were rinsed four times in absolute ethanol and dried under a steam of Nitrogen. 3) The amino-modified gold slides were dipped into a solution (50–100 uM) of succinimidyl 4-(N-maleimidomethyl)-cyclohexane-1-carboxylate (SMCC) to render a surface that presents the maleimide functional groups.

Aluminum slides were made or purchased from Amersham-Pharmacia, coated with a 1000–1400 Angstrom layer of silicon oxide, and a layer of aminopropysilane (APS). The amino-modified Al surfaces are functionalized with SMCC as described above.

In some cases, after spotting the peptoid library, the aluminum slides were etched in a solution of 0.1% SDS/5× SSC at 60 degrees C. for 2 hours. The etched slides exhibit a reduced oxide layer thickness (200–900 Angstroms) to allow amplification of both the Cy5 and Cy3 signals.

Example 3

Derivatization of Aluminum/$SiO_2$ Surfaces with Avidin

Aluminum slides coated with aminosilane were dipped into a solution of NHS-LC-LC-biotin ("LC" refers to 6-aminohexanoyl and "NHS" refers to N-hydroxysuccinimidyl) (commercially available from Pierce), depicted in FIG. 7A, that was 0.39 mM in PBS buffer. The slides were coated for 1.5 hours with shaking at 80 rpm. After attachment of biotin, the slides were rinsed with water, then dipped in a solution of 1 ug/ml–1 mg/ml avidin, streptavidin or neutravidin in PBS buffer for 2 hours, stirring at 70 rpm. The slides were rinsed with water and ready for spotting biotinylated peptides or peptoids. FIG. 7B depicts a representation of an avidin-derviatized aluminum slide spotted with a biotinylated protein-binding agent in accordance with one embodiment of the present invention.

The various surface modification steps was followed using ellipsometry to note the thickness changes. A thickness change increase of 40–45 angstroms was reproducibly recorded after the addition of avidin to the surface layers.

Example 4

Protein Labeling

Protein solutions were adjusted to a concentration of 1 mg/mL in 0.1 M sodium carbonate, pH 9.3 and a volume of 0.1–1 mL, and mixed with bifunctional or mono-functional amine-reactive cyanine dye (Cy3 or Cy5, Amersham Pharmacia). The protein was purified from the unreacted dye by size exclusion chromatography using a Sephadex G-25 packing in a 5 cm long, 1.7 cm diameter column with a 1 mL load, 0.5 mL fractions, and a dilution factor of 3.5.

Figure 8:
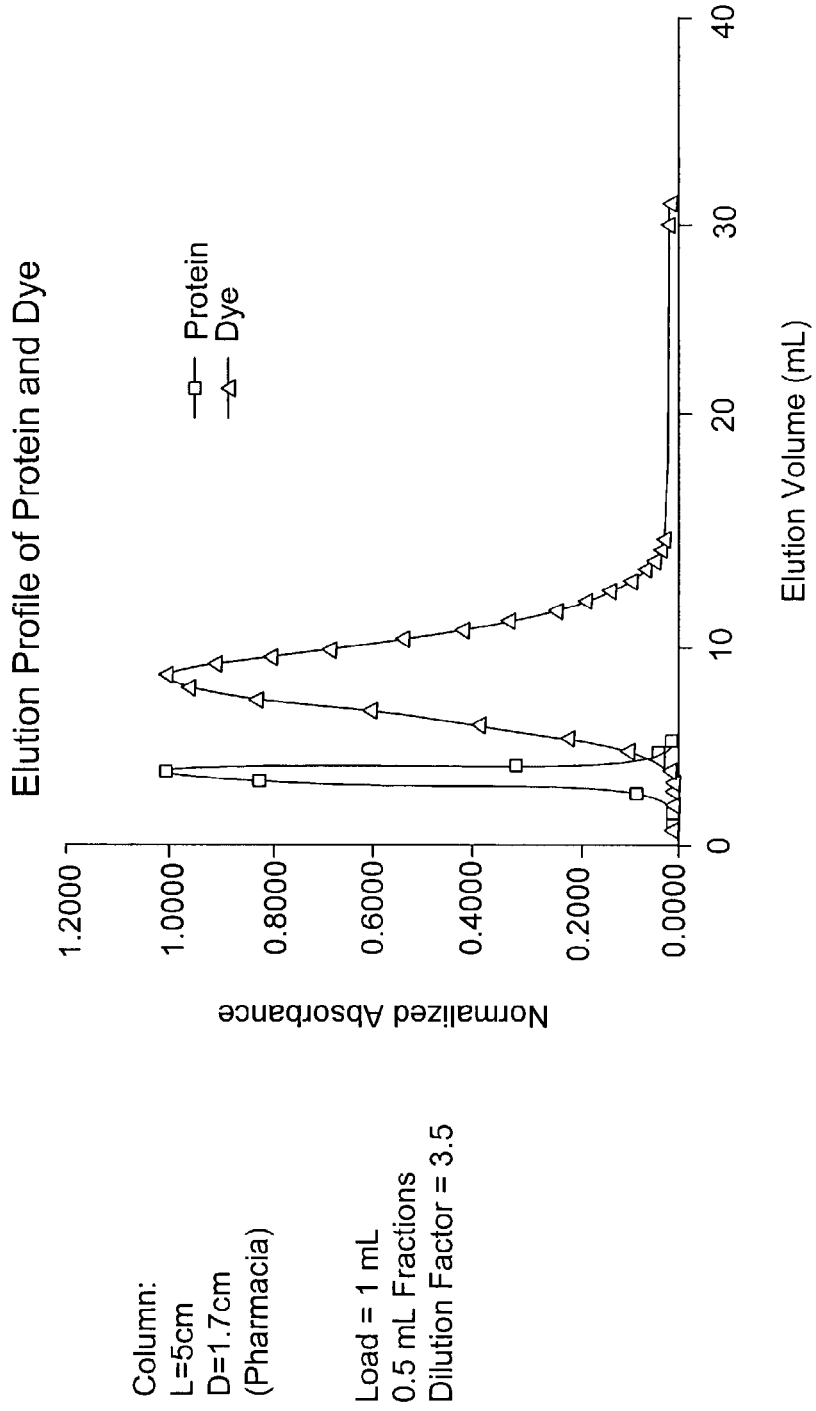
FIG. 8 depicts a graph of results of size exclusion chromatography conducted to separate labeled protein from the unreacted dye prior to application of the labeled protein sample to a microarray in accordance with embodiments of the present invention.

FIG. 8 provides a graph of the results illustrating that size exclusion chromatography of the components efficiently separates the labeled protein from the unreacted dye. The graph shows the different elution profiles for the protein (BSA standard) and dye molecules.

Example 5

Chip Binding Experiments

In some instances, the chips spotted with the peptoid library are chemically blocked with cysteine, mercaptoethanol or other suitable hydrophilic thiol. The chips are blocked with protein such as 2% BSA/PBS, 10% non-fat dry milk or 1% casein for at least 1 hour, rinsed with water and dried. The labeled protein probe solution is diluted accordingly (typically to 20–1000 ng total protein) with the blocking solution (for the etched Al slides, detection limits of a few picograms have been observed). A 30–100 L aliquot of the probe solution is applied to the chip surface, and a clean coverslip placed on top, forming a sandwich of the probe solution on the chip surface. The protein solution is incubated with the chip for at least 1 hour. The coverslip is removed in 1×PBS/0.05% Tween or other suitable buffer containing surfactant. The chip is then washed in 1×PBS/0.05% Tween or other suitable buffer/surfactant system. The chips are further rinsed with water, dried under a stream of Argon or Nitrogen and scanned.

Example 6

Sample Chip

Figure 9:
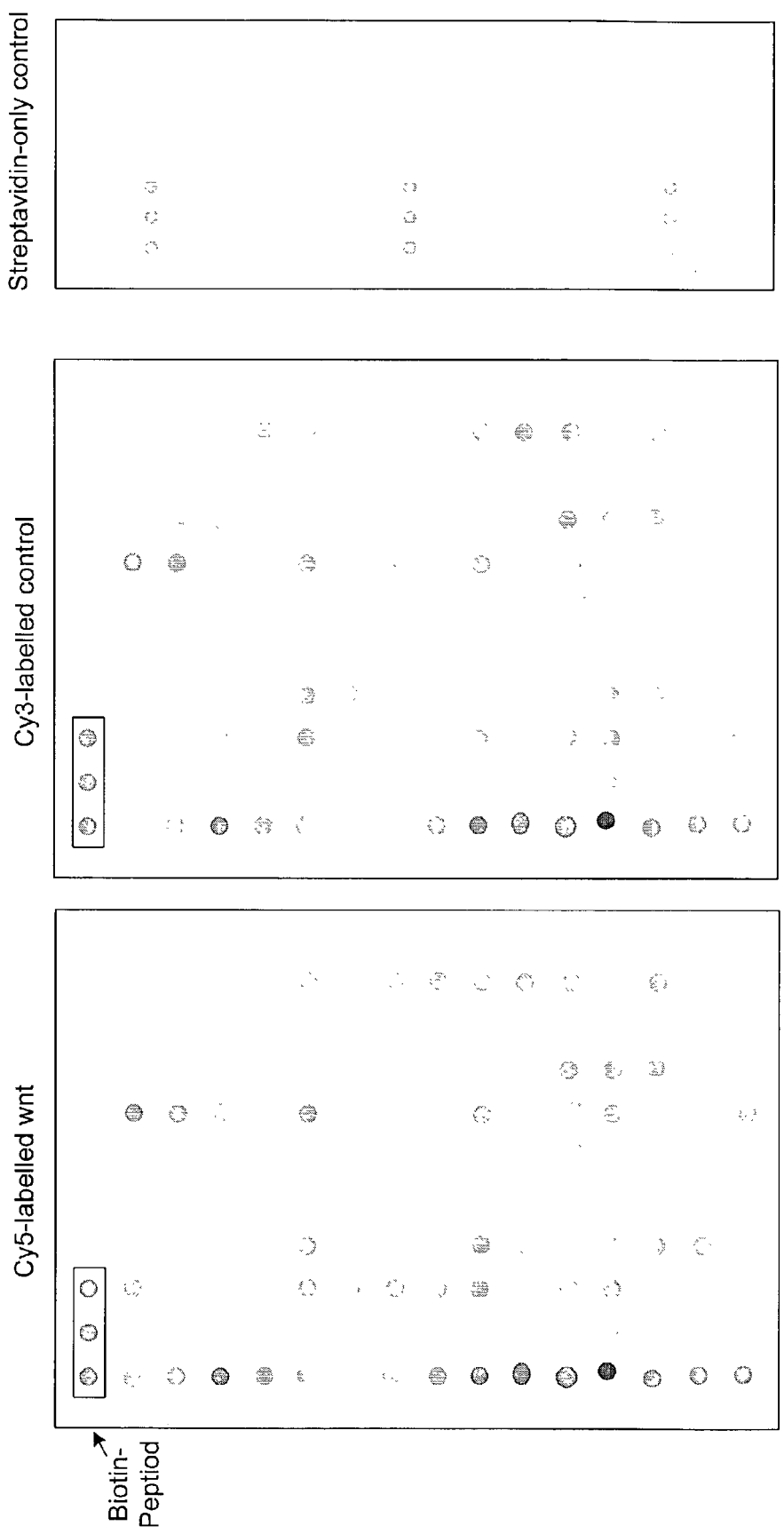
FIGS. 9A–9C depict scans of microarray chips bearing a library of 1,000 peptoid-based protein-binding agents used to prove the concept of the present invention.

A microarray chip bearing a library of 1,000 peptoid-based protein-binding agents was prepared in accordance with the present invention. Streptavidin was spiked into cells induced to express proteins in the wnt pathway and into control cell lysate and the entire mixture labeled with Cy3 (control) or Cy5 (wnt). The mixture was then incubated with the chip (6.3 ng total protein/chip; 31 pg streptavidin/chip), which had a biotin-displaying peptoid in it's upper left corner. FIGS. 9A and 9B show ⅙ of the incubated chip. As shown, in addition to the biotin peptoid spots, many other peptoid spots are binding to the protein in the lysate. By comparing the relative signals from the Cy5 and Cy3 channels, differentials can be identified. FIG. 9C shows ½ of a streptavidin-only control chip (31 pg streptavidin/chip). Biotin peptoid spots are visible in the upper left corner.

Example 7

Demonstration Chip

Figure 10:
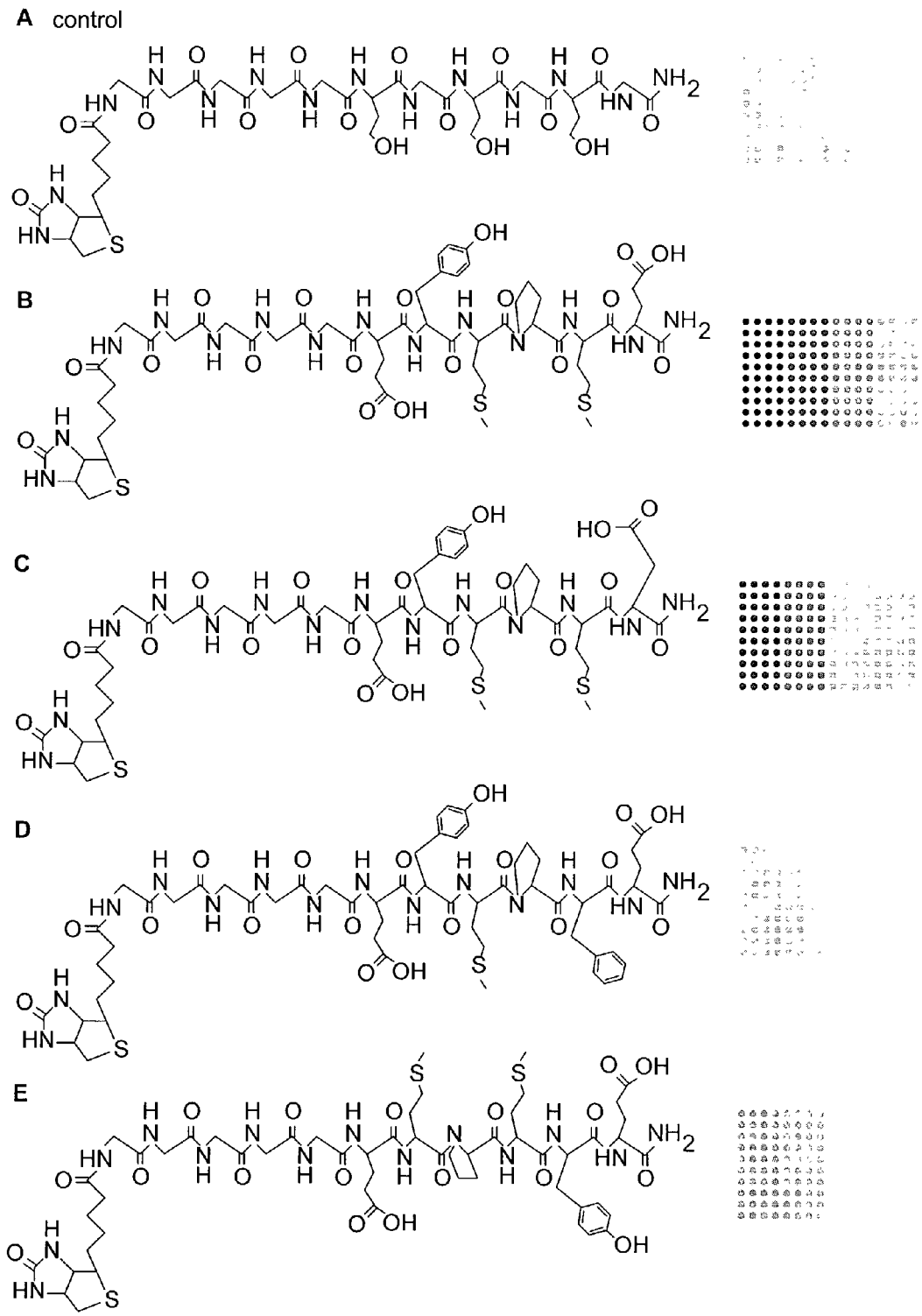
FIG. 10 depicts biotinylated hexameric peptides (A through E) and the corresponding signal intensity obtained when the biotinylated peptides were spotted onto avidin-treated slides, blocked with casein, and probed with Cy5-labelled antiglu antibodies.

As illustrated in FIG. 10, hexameric peptides of different and known affinity to the "anti-glu" antibody were synthesized with a biotin anchoring group and heptameric gycyl linker. To prove the concept of the present invention, the biotinylated peptides were spotted onto avidin-treated slides as described in the present disclosure. The slides were blocked with casein and probed with Cy5-labelled antiglu antibodies. The gradations in signal intensity correlate with the known differences (e.g., measured by direct ELISA) in affinity between the peptides and their cognate antibody probe.

Example 8

Comparison of Surface Attachment Systems

FIG. 11 depicts the dependence of signal strength on the mode of surface attachment of a protein-binding agent to a substrate. In this example, signal increases of 1000× are observed for biotin/avidin immobilization compared to thiol/maleimide (signal results depicted above surface attachment description and molecular structure).

Example 9

Preparation of Protein-Coated Slide Surface for Antibody Display

To prepare Protein A- or Protein G-modified side surfaces, a slide coated with avidin (prepared as described above) was immersed in a solution of biotinylated Protein A or Protein G (0.5–1 mg/mL in PBS buffer, purchased from Pierce, product numbers 29989zz and 29988zz) for 2 hours at room temperature. The slides were then rinsed with de-ionized distilled water and blown dry with Nitrogen or Argon.

Example 10

Comparison of Glass and Mirrored Slides

Al/SiO2/APTES slides were purchased from Amersham-Pharmacia, or home-made in a Class 100 cleanroom. Slides were prepared with a reflective aluminum coating that is further overcoated with a thin silicon dioxide dielectric, followed by APTES. The homemade slides were pre-cleaned by sonication in a liquid surfactant for 10 minutes, rinsed with de-ionized water, then further cleaned in a solution of Nochromix/H2SO4. Following a de-ionized water rinse, the slides were immersed in isopropanol for 5 minutes and dried. A Model CH-SEC-600-RAP e-beam equipped with rotating planetaries was pumped to 2×10-6 torr prior to deposition of 1000 A of aluminum and 800 A of SiO2 (brand names). The slides were then placed in a vacuum oven at 100 containing 25 mL of APTES, and pressure reduced to −23 mm Hg. The slides were used without further treatment. cDNA clones were robotically spotted from 1:1 water/DMSO solution onto the substrates using a Generation III Molecular Dynamics Spotter.

FIG. 12 shows a comparison of the image obtained from an APTES-coated glass microscope slide to that of an APTES-coated aluminum slide. The same amount of fluorescently labeled analyte sample was applied to each surface. Although different input mRNA was used, the top row depicts a standard set of spiked controls. Spot 1, arabidopsis mRNA is spiked in at 25 ng for the Al slide and 250 ng for the glass slide, yet the signal is 2 times greater for the aluminum slide. The second spot of the top row is spiked at the equivalent of 1 copy per cell. On the glass substrate, the signal is barely detectable compared to a robust signal that is about 20 times greater using the Al substrate. Background non-specific binding is minimal in both cases, as shown by the clear background for spots 20–22 (bacterial genes) and spots 26–29 (DMSO) and spots 31–33 (drosophila genes). The Al/SiO$_2$ substrate amplifies the signal from Cy3/Cy5 tagged cDNA by approximately 10–40 fold relative to the corresponding glass substrate.

Thus, the Al/SiO$_2$ (mirrored) slides yield array images that are superior to their plain-glass counterparts with respect to signal strength, as well as spot morphology and uniformity.

Conclusion

Although the foregoing invention has been described in some detail for purposes of clarity of understanding, it will be apparent that certain changes and modifications may be practiced within the scope of the invention. For example, while the present disclosure emphasizes the use of peptoids as the peptidomimetic segment of the protein-binding array elements, it should be understood that the scope of the invention is not so limited and other molecules having the appropriate properties and function as described herein may also be used. It should also be noted that there are many alternative ways of implementing both the process and apparatus of the present invention. Accordingly, the present embodiments are to be considered as illustrative and not restrictive, and the invention is not to be limited to the details given herein.

What is claimed is:

1. An array of protein-binding agents stably attached to the surface of a solid substrate, said array comprising:
   a solid substrate having a substantially planar surface comprising an organic chemically-modified dielectric-coated reflective metal;
   a plurality of protein-binding agents bound to said substrate, each of said protein-binding agents comprising,
      an anchoring segment stably bound to the substrate surface,
      a peptidomimetic protein-binding segment, and
      a linker segment connecting and separating the anchoring and peptidomimetic segments; and
   a di-thiol modified polyethylene glycol non-protein chemical blocking agent and a protein blocking agent bound to the substrate surface not occupied by protein-binding agent array elements bound to the substrate surface.

2. The array of claim 1, wherein said substrate comprises an organic chemically-modified dielectric-coated reflective metal on glass surface beneath said anchoring segment.

3. The array of claim 2, wherein said metal is one aluminum, gold, or titanium.

4. The array of claim 2, wherein said metal is aluminum, said dielectric is SiO$_2$ and said organic chemical modification is an aminosilane.

5. The array of claim 4, wherein said aminosilane is functionalized with a maleimide.

6. The array of claim 2, wherein said peptidomimetic segment is a peptoid.

7. The array of claim 2, wherein said linker segment is selected from the group consisting of C2–C100 aliphatic chains, polyethylene oxide, and orthogonal peptidomimetic or peptide oligomers.

8. The array of claim 2, wherein said anchoring segment is a thiol.

9. The array of claim 1, wherein the protein blocking agent is selected from the group consisting of casein, non-fat milk and BSA.

10. A kit for use in performing a differential binding assay, said kit comprising:
    an array comprising,
       a solid substrate having a substantially planar surface comprising an organic chemically-modified dielectric-coated reflective metal;
       a plurality of protein-binding agents bound to said substrate, each of said protein-binding agents comprising,
          an anchoring segment stably bound to the substrate surface,
          a peptidomimetic protein-binding segment, and
          a linker segment connecting and separating the anchoring and peptidomimetic segments;
       a di-thiol modified polyethylene glycol non-protein chemical blocking agent and a protein blocking agent bound to the substrate surface not occupied by protein-binding agent array elements bound to the substrate surface; and
    binding assay reagents.

11. The kit of claim 10, wherein in the array the metal is aluminum, the dielectric is SiO$_2$ and said modifying organic chemical is an aminosilane.

12. The kit of claim 11, wherein the aminosilane is functionalized with a maleimide.

13. The kit of claim 12, wherein in the array the peptidomimetic segment is a peptoid.

14. The kit of claim 10, wherein the protein blocking agent is selected from the group consisting of casein, non-fat milk and BSA.

15. The kit of claim 10, wherein the protein blocking agent is casein.

16. The kit of claim 10, wherein in the array the metal is aluminum disposed on a glass slide and the SiO$_2$ coating is about 800 angstrom thick silicon dioxide.

17. The array of claim 1, wherein in the array the metal is aluminum disposed on a glass slide and the SiO$_2$ coating is about 800 angstrom thick silicon dioxide.

18. The array of claim 9, wherein the protein blocking agent is casein.

* * * * *